(12) United States Patent
Bedell et al.

(10) Patent No.: US 6,656,954 B2
(45) Date of Patent: Dec. 2, 2003

(54) SULFONYL DIVALENT ARYL OR HETEROARYL HYDROXAMIC ACID COMPOUNDS

(75) Inventors: Louis J. Bedell, Mt. Prospect, IL (US); Joseph J. McDonald, Ballwin, MO (US); Thomas E. Barta, Evanston, IL (US); Daniel P. Becker, Glenview, IL (US); Shashidhar N. Rao, St. Louis, MO (US); John N. Freskos, Clayton, MO (US); Brent V. Mischke, Defiance, MO (US); Daniel P. Getman, Chesterfield, MO (US); Gary A. DeCrescenzo, St. Charles, MO (US)

(73) Assignee: Pharmacia Corporation, Skokie, IL (US)

( * ) Notice: Subject to any disclaimer, the term of this patent is extended or adjusted under 35 U.S.C. 154(b) by 2 days.

(21) Appl. No.: 09/997,552

(22) Filed: Nov. 29, 2001

(65) Prior Publication Data

US 2002/0103239 A1 Aug. 1, 2002

Related U.S. Application Data

(62) Division of application No. 09/230,209, filed as application No. PCT/US98/04300 on Mar. 4, 1998, now Pat. No. 6,380,258.
(60) Provisional application No. 60/035,182, filed on Mar. 4, 1997.

(51) Int. Cl.$^7$ ................ A61K 31/445; C07D 401/10

(52) U.S. Cl. ............... 514/318; 514/235.5; 514/256; 514/278; 514/316; 514/320; 514/321; 514/326; 514/336; 514/357; 514/365; 514/366; 514/374; 514/375; 514/378; 514/397; 514/398; 514/399; 544/129; 544/238; 544/310; 544/365; 546/19; 546/186; 546/189; 546/193; 546/194; 546/197; 546/210

(58) Field of Search ................ 514/235.5, 256, 514/278, 316, 318, 320, 321, 326, 336, 357, 365, 366, 374, 375, 378, 397, 398, 399; 544/129, 230, 365, 310; 546/186, 189, 193, 194, 197, 210, 19

(56) References Cited

U.S. PATENT DOCUMENTS

| | | | |
|---|---|---|---|
| 4,148,801 A | 4/1979 | Santilli et al. | 548/131 |
| 4,595,700 A | 6/1986 | Donald et al. | 514/616 |
| 5,103,014 A | 4/1992 | Musser et al. | 548/204 |
| 5,424,279 A | 6/1995 | Sugai et al. | 504/282 |
| 5,455,258 A | 10/1995 | MacPherson et al. | 514/336 |
| 5,506,242 A | 4/1996 | MacPherson et al. | 514/336 |
| 5,552,419 A | 9/1996 | MacPherson et al. | 514/357 |
| 5,646,167 A | 7/1997 | MacPherson et al. | 514/357 |
| 5,932,595 A | 8/1999 | Bender et al. | 514/317 |
| 6,380,258 B2 | 4/2002 | Bedell et al. | 514/575 |
| 2001/0014688 A1 * | 8/2001 | Barta et al. | 514/318 |

FOREIGN PATENT DOCUMENTS

| | | | |
|---|---|---|---|
| DE | DE 3738890 | 5/1989 | C07C/83/10 |
| EP | 0 780 386 | 6/1997 | C07D/309/08 |
| EP | 0 853 255 | 7/1998 | G03C/1/498 |
| WO | WO 90/05719 | 5/1990 | C07C/323/62 |
| WO | WO 93/20047 | 10/1993 | C07C/317/44 |
| WO | WO 94/02466 | 2/1994 | C07D/221/14 |
| WO | WO 94/24140 | 10/1994 | C07H/13/04 |
| WO | WO 95/09841 | 4/1995 | C07C/323/60 |
| WO | WO 95/13289 | 5/1995 | C07K/5/062 |
| WO | WO 95/29892 | 11/1995 | C07D/207/327 |
| WO | WO 96/06074 | 2/1996 | C07C/259/06 |
| WO | WO 96/11209 | 4/1996 | C07K/5/06 |
| WO | WO 97/20824 | 6/1997 | C07D/241/04 |
| WO | WO 97/24117 | 7/1997 | A61K/31/19 |
| WO | WO 97/49679 | 12/1997 | C07C/317/44 |
| WO | WO 98/37877 | 9/1998 | A61K/31/16 |

OTHER PUBLICATIONS

Morrison and Boyd "Organic chemistry" Allyn and Bancon, p.326 (1973).*
Wilbrahan et al. "Organic and biological chemistry" Souten III. Univ. p.250–251 (1985).*
Rubini et al. "Synthetic of isosteric methylene–oxy . . . " Tetrahedron v. 21, p. 6039–45 (1986).*
U.S. patent application Ser. No. 09/569,034, Bedell et al., filed May 11, 2000.
U.S. patent application Ser. No. 09/728,408, Bedell et al., filed Dec. 1, 2000.
U.S. patent application Ser. No. 09/909,227, Barta et al., filed Jul. 19, 2001.
Cramp et al., *Preparation of hydroxybenzophenones as herbicides*, CA 128:257232 (1998).
Denis et al., *Matrix metalloproteinase inhibitors: Present achievements and future prospects*, Invest. New Drugs, 15:175 185 (1997).
Fujisawa et al., *Preparation of N–[4–(hydroxyamino)succinyl]amino acid amide derivatives as metalloproteinase inhibitors*, CA 131:73975 (1999).
Gearing et al., *Processing of tumour necrosis factor–α precursor by metalloproteinases*, Nature, 370:555–557 (1994).
Hannout et al., *Synthesis and screening of some new methyl salicylate–5–sulfonamides containing active units as analgesic agents*, J. Serb. Chem. Soc. 53(7):353–361 (1988).

(List continued on next page.)

Primary Examiner—Ceila Chang
(74) Attorney, Agent, or Firm—Philip B. Polster, II; Julie M. Chappell

(57) ABSTRACT

A sulfonyl divalent aromatic or heteroaromatic ring hydroxamic acid compound that inter alia inhibits matrix metalloprotease activity is disclosed as are a treatment process that comprises administering a contemplated sulfonyl divalent aromatic or heteroaromatic ring hydroxamic acid compound in a MMP enzyme-inhibiting effective amount to a host having a condition associated with pathological matrix metalloprotease activity.

25 Claims, No Drawings

OTHER PUBLICATIONS

Kenyon et al., *A model of angiogenesis in the mouse cornea*, Invest. Ophthalmol. Vis. Sci., 37(8):1625–1632 (1996).

Knight et al., *A novel coumarin–labelled peptide for sensitive continuous assays of the matrix metalloproteinases*, Febs Lett. 296(3):263–266 (1992).

McGeehan et al., *Regulation of tumour necrosis factor–α processing by a metalloproteinase inhibitor*, Nature, 370:558–561 (1994).

Mitchell et al., *Cloning, expression, and type II collagenolytic activity of matrix metalloproteinase–13 from human osteoarthritic cartilage*, J. Clin. Invest., 97(3):761–768 (1996).

Rasmussen et al., *Matrix metalloproteinase inhibition as a novel anticancer strategy: a review with special focus on batimasat and marimastat*, Pharmacol. Ther., 75(1):69–75 (1997).

Reboul et al., *The new collagenase, collagenase–3, is expressed and synthesized by human chondrocytes but not by synoviocytes*, J. Clin. Invest., 97(9):2011–2019 (1996).

Schwartz et al., *Synthetic inhibitors of bacterial and mammalian interstitial collagenases*, Prog. In Med. Chem., 29:271–334 (1992).

Young et al., *2–Heterocyclic indole–3–sulfones as inhibitors of HIV–1 reverse transcriptase*, CA 123:83233 (1995).

\* cited by examiner

SULFONYL DIVALENT ARYL OR HETEROARYL HYDROXAMIC ACID COMPOUNDS

PRIORITY CLAIM TO RELATED PATENT APPLICATION

This patent claims priority as a divisional application to U.S. patent application Ser. No. 09/230,209 (filed Jun. 24, 1999) now U.S. Pat. No. 6,380,258, which, in turn, is a 371 of PCT Patent Application No. PCT/US98/04300 (filed Mar. 4, 1998), which, in turn, claims priority to U.S. Patent Provisional Application Serial No. 60/035,182 (filed Mar. 4, 1997). The entire test of those patent applications is incorporated by reference into this patent.

DESCRIPTION

TECHNICAL FIELD

This invention is directed to proteinase (protease) inhibitors, and more particularly to sulfonyl divalent aryl or heteroaryl hydroxamic acid compounds that, inter alia, inhibit the activity of matrix metalloproteinases, compositions of those inhibitors, intermediates for the syntheses of those compounds, processes for the preparation of the compounds and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; coronary thrombosis and bone disease. Defective injury repair processes can also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-α. Inhibition of TNF-α convertase inhibits production of active TNF-α. Compounds that inhibit both MMPs activity have been disclosed in WIPO International Publication Nos. WO 94/24140, WO 94/02466 and WO 97/20824. There remains a need for effective MMP and TNF-α convertase inhibiting agents. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)).

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and as yet not associated with any pathological condition. The disclosure that follows describes one family of hydroxamate MMP inhibitors that exhibit those desirable activities

BRIEF SUMMARY OF THE INVENTION

The present invention is directed to a family of molecules that among other properties inhibit matrix metalloprotease (MMP) activity, and particularly inhibit the activity of one or more of MMP-2, MMP-9, or MMP-13, while generally exhibiting little activity against MMP-1. The present invention is also directed to processes for preparing a contemplated compound and for treating a mammal having a condition associated with pathological matrix metalloprotease activity.

Briefly, one embodiment of the present invention is directed to a sulfonyl divalent aryl or heteroaryl hydroxamic acid compound that can act as a matrix metalloprotease enzyme inhibitor. That compound corresponds in structure to Formula I.

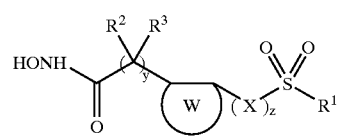

wherein y and z are each zero or one and the sum of z+y is one;

the ring structure W is a 5- or 6-membered divalent aromatic or heteroaromatic ring;

X is —CH$_2$— or —NH—;

R$^1$ is a substituent containing a 5- or 6-membered cyclohydrocarbyl, heterocyclo, aryl or heteroaryl radical bonded directly to the depicted SO$_2$-group and having a length greater than about that of a hexyl group and less than about that of a eicosyl group, said R$^1$ defining a three-dimensional volume, when rotated about an axis drawn through the SO$_2$-bonded 1-position and the 4-position of a 6-membered ring radical or drawn through the SO$_2$-bonded 1-position and the center of 3,4-bond of a 5-membered ring radical, whose widest dimension in a direction transverse to the axis of rotation is about that of one furanyl ring to about that of two phenyl rings;

R$^2$ and R$^3$ are independently hydrido, C$_1$–C$_4$ hydrocarbyl, hydroxyl or amino, or R$^2$ and R$^3$ together with the depicted carbon atom to which they are bonded form a 6-membered heterocyclic ring in which the heteroatom is oxygen, sulfur or nitrogen, said heteroatom being optionally substituted with one or two oxygens when sulfur and being optionally substituted with a moiety selected from the group consisting of a C$_1$–C$_4$ hydrocarbyl, C$_3$–C$_6$ cyclohydrocarbyl, C$_1$–C$_4$ acylhydrocarbyl, and sulfonyl C$_1$–C$_4$ hydrocarbyl group when nitrogen.

In preferred embodiments, a contemplated compound corresponds in structure to Formula IA,

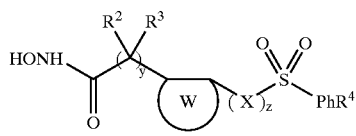

IA wherein W, X, y, z, $R^2$ and $R^3$ are as defined above, Ph is phenyl substituted at the 4-position with substituent $R^4$ that is defined hereinafter.

A process for treating a host mammal having a condition associated with pathological matrix metalloprotease activity is also contemplated. That process comprises administering a compound described hereinbefore in an enzyme-inhibiting effective amount to a mammalian host having such a condition. The use of repeated administrations is particularly contemplated.

Among the several benefits and advantages of the present invention are the provision of compounds and compositions effective as inhibitors of matrix metalloproteinase activity, and the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of a method for preparing such compositions. Another benefit is the provision of a method for treating a pathological condition associated with abnormal matrix metalloproteinase activity.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Still further benefits and advantages of the invention will be apparent to the skilled worker from the disclosure that follows.

DETAILED DESCRIPTION OF PREFERRED EMBODIMENTS

In accordance with the present invention, it has been found that certain sulfonyl divalent aryl or heteroaryl hydroxamic acids (hydroxamates) are effective, inter alia, for inhibition of matrix metalloproteinases ("MMPs") believed to be associated with uncontrolled or otherwise pathological breakdown of connective tissue. In particular, it has been found that these certain sulfonyl divalent aryl or heteroaryl hydroxamic acid compounds are effective for inhibition of collagenase III (MMP-13) and also gelatinase A (MMP-2), which can be particularly destructive to tissue if present or generated in abnormal quantities or concentrations, and thus exhibit a pathological activity.

Moreover, it has been discovered that many of these aromatic sulfonyl alpha-cycloamino hydroxamic acids are selective in the inhibition of MMPs associated with diseased conditions without excessive inhibition of other collagenases essential to normal bodily function such as tissue turnover and repair. More particularly, it has been found that particularly preferred the sulfonyl divalent aryl or heteroaryl hydroxamic acid compounds are particularly active in inhibiting of MMP-13 and/or MMP-2, while having a limited or minimal effect on MMP-1. This point is discussed in detail hereinafter and is illustrated in the Inhibition Table hereinafter.

One embodiment of the present invention is directed to a sulfonyl divalent aryl or heteroaryl hydroxamic acid compound that can act as a matrix metalloprotease enzyme inhibitor. That compound corresponds in structure to Formula I

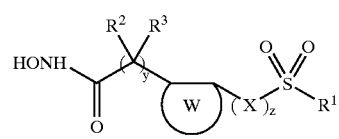

I wherein
y and z are each zero or one and the sum of z+y is one;
the ring structure W is a 5- or 6-membered divalent aromatic or heteroaromatic ring;
X is —$CH_2$— or —NH—;
$R^1$ is a substituent containing a 5- or 6-membered cyclohydrocarbyl, heterocyclo, aryl or heteroaryl radical bonded directly to the depicted $SO_2$-group and having a length equivalent to a length that is greater than about that of a fully extended hexyl group and less than about that of a fully extended eicosyl group, said $R^1$ defining a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings;
$R^2$ and $R^3$ are independently hydrido, $C_1$–$C_4$ hydrocarbyl, hydroxyl or amino, or $R^2$ and $R^3$ together with the depicted carbon atom to which they are bonded form a 6-membered heterocyclic ring in which the heteroatom is oxygen, sulfur or nitrogen, said heteroatom being optionally substituted with one or two oxygens when sulfur and being optionally substituted with a moiety selected from the group consisting of a $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl group when nitrogen.

In the above structural formula and other formulas herein, one of y and z is one and the other is zero so that the sum of y plus z is one. Thus, either the —$CR^2R^3$— or the —$CH_2$— group of such formulas is absent in each contemplated compound.

The ring structure W is a 5- or 6-membered divalent aromatic or heteroaromatic ring in which the depicted —$CR^2R^3$— and —$CH_2$— groups are bonded to adjacent carbon atoms of the aryl or heteroaryl ring. As a consequence, the hydroxamate carbonyl group and the $R^1$-linked sulfonyl group are separated by three carbon atoms in each contemplated compound.

Contemplated divalent aromatic or heteroaromatic rings include 1,2-phenylene, 2,3-pyridinylene, 3,4-pyridinylene, 4,5-pyridinylene, 2,3-pyrazinylene, 4,5-pyrimidinylene, and 5,6-pyrimidinylene groups. 1,2-Phenylene is a particularly preferred divalent aromatic or heteroaromatic ring, and is used illustratively herein as W.

As noted above, an $R^1$ substituent contains a 5- or 6-membered cyclohydrocarbyl, heterocyclo, aryl or heteroaryl radical bonded directly to the depicted $SO_2$-group. An $R^1$ substituent also has length, width and substitution requirements that are discussed in detail below. It is noted here, however, that a single-ringed or fused ring cyclohydrocarbyl, heterocyclo, aryl or heteroaryl radical is not itself long enough to fulfill the length requirement. As such, that cyclohydrocarbyl, heterocyclo, aryl or heteroaryl radical must itself be substituted.

Exemplary 5- or 6-membered cyclohydrocarbyl, heterocyclo, aryl or heteroaryl radicals that can constitute a portion of a $R^1$ substituent and are themselves substituted as discussed herein include phenyl, 2-, 3-, or 4-pyridyl, 2-naththyl, 2-pyrazinyl, 2- or 5-pyrimidinyl, 2- or 3-benzo (b)thienyl, 8-purinyl, 2- or 3-furyl, 2- or 3-pyrrolyl, 2-imidazolyl, cyclopentyl, cyclohexyl, 2- or 3-piperidinyl, 2- or 3-morpholinyl, 2- or 3-tetrahydropyranyl, 2-imidazolidinyl, 2- or 3-pyrazolidinyl and the like. A phenyl radical is particularly preferred and is used illustratively herein.

When examined along its longest chain of atoms, an $R^1$ substituent, including its own substituent when present, has a total length equivalent to a length that is greater than that of a fully extended saturated chain of six carbon atoms (a hexyl group); i.e., a length of a heptyl chain or longer, and a length that is less than that of a fully extended saturated chain of about 20 carbons (an eicosyl group). Preferably, that length is about 8 to about 18 carbon atoms, even though many more atoms may be present in ring structures or substituents. This length requirement is discussed further below.

Looked at more generally, and aside from specific moieties from which it is constructed, an $R^1$ substituent (radical, group or moiety) has a length of a heptyl group or greater. Such an $R^1$ substituent also has a length that is less than that of an eicosyl group. That is to say that a $R^1$ is a substituent having a length greater than that of a fully extended saturated six carbon chain and shorter than that of a fully extended saturated twenty carbon chain, and more preferably, a length greater than that of a octyl group and less than that of a palmityl group. The radical chain lengths are measured along the longest linear atom chain in the radical, following the skeletal atoms of a ring where necessary. Each atom in the chain, e.g. carbon, oxygen or nitrogen, is presumed to be carbon for ease in calculation.

Such lengths can be readily determined by using published bond angles, bond lengths and atomic radii, as needed, to draw and measure a chain, or by building models using commercially available kits whose bond angles, lengths and atomic radii are in accord with accepted, published values. Radical (substituent) lengths can also be determined somewhat less exactly by presuming, as is done here, that all atoms have bond lengths of saturated carbon, that unsaturated and aromatic bonds have the same lengths as saturated bonds and that bond angles for unsaturated bonds are the same as those for saturated bonds, although the above-mentioned modes of measurement are preferred. For example, a 4-phenyl or 4-pyridyl group has a length of a four carbon chain, as does a propoxy group, whereas a biphenyl group has a length of about an eight carbon chain using a contemplated measurement mode.

In addition, an $R^1$ substituent, when rotated about an axis drawn through the $SO_2$-bonded 1-position and the 4-position of a 6-membered ring radical or the $SO_2$-bonded 1-position and through the 3,4 bond of a 5-membered ring radical defines a three-dimensional volume whose widest dimension has the width of about one furanyl ring to about the width of two phenyl rings in a direction transverse to that axis to rotation.

When utilizing this width or volume criterion, a fused ring system such as a naphthyl or purinyl radical is considered to be a 6- or 5-membered ring that is substituted at appropriate positions numbered from the $SO_2$-linkage that is deemed to be at the 1-position as discussed before. Thus, a 2-naphthyl substituent or an 8-purinyl substituent is an appropriately sized $R^1$ radical as to width when examined using the above rotational width criterion. On the other hand, a 1-naphthyl group or a 7- or 9-purinyl group is too large upon rotation and is excluded.

As a consequence of these length and width requirements, $R^1$ substituents such as 4-(phenyl)phenyl [biphenyl], 4-(4'-methoxyphenyl)phenyl, 4-(phenoxy)phenyl, 4-(thiophenyl) phenyl [4-(phenylthio)phenyl], 4-(phenylazo)phenyl 4-(phenylureido)phenyl, 4-(anilino)phenyl, 4-(nicotinamido)phenyl, 4-(isonicotinamido)phenyl, 4-(picolinamido)phenyl and 4-(benzamido)phenyl are among particularly preferred $R^1$ substituents, with 4-(phenoxy)phenyl and 4-(thiophenyl)phenyl being most preferred.

An $SO_2$-linked cyclohydrocarbyl, heterocyclo, aryl or heteroaryl radical is a 5- or 6-membered single-ring that is itself substituted with one other substituent, $R^4$. The $SO_2$-linked single-ringed cyclohydrocarbyl, heterocyclo, aryl or heteroaryl radical is $R^4$-substituted at its own 4-position when a 6-membered ring and at its own 3-position when a 5-membered ring. The cyclohydrocarbyl, heterocyclo, aryl or heteroaryl radical to which $R^4$ is bonded is preferably a phenyl group, so that $R^1$ is preferably $PhR^4$ in which $R^4$ is bonded at the 4-position of the $SO_2$-linked phenyl (Ph) radical, and in which $R^4$ can itself be optionally substituted as is discussed hereinafter. Substitution at the 2-position of a $SO_2$-linked cyclohydrocarbyl, heterocyclo, aryl or heteroaryl radical appears to greatly lessen inhibitory potency toward MMP enzymes, and is absent from a contemplated compound.

A contemplated $R^4$ substituent can be a single-ringed cyclohydrocarbyl, heterocyclo, aryl or heteroaryl group or another substituent having a chain length of 3 to about 14 carbon atoms such as a hydrocarbyl or hydrocarbyloxy group [e.g., $C_3$–$C_{14}$ hydrocarbyl or O—$C_2$–$C_{14}$ hydrocarbyl], a phenyl group, a phenoxy group [—$OC_6H_5$], a thiophenoxy group [phenylsulfanyl; —$SC_6H_5$], an anilino group [—$NHC_6H_5$], a phenylazo group [—$N_2C_6H_5$], a phenylureido group [aniline carbonylamino; —NHC(O)NH—$C_6H_5$], a benzamido group [—NHC(O)$C_6H_5$], a nicotinamido group [3-NHC(O)$C_5H_4$N], an isonicotinamido group [4-NHC(O)$C_5H_4$N], or a picolinamido group [2-NHC(O)$C_5H_4$N]. As noted before in conjunction with the discussion of $R^1$, most preferred $R^4$ substituents are phenoxy and thiophenoxy groups that are preferably themselves free of substitution. Additionally contemplated $R^4$ substituent groups include a heterocyclo, heterocyclohydrocarbyl, arylhydrocarbyl, arylheterocyclohydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, or a heteroarylthio group.

A contemplated $R^4$ substituent can itself also be substituted with one or more substituent radicals at the meta- or para-position or both of a six-membered ring with a single atom or a substituent containing a longest chain of up to ten atoms, excluding hydrogen. Exemplary substituent radicals include a halo, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonyl-hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino and N-monosubstituted or N,N-disubstituted aminohydrocarbyl group wherein the substituent(s) on the nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the nitrogen and two substituents attached thereto form a 5- to 8-membered heterocyclic or heteroaryl ring group.

Thus, initial studies indicate that so long as the length, substitution and width (volume upon rotation) requirements of an $SO_2$-linked $R^1$ substituent discussed herein are met, an $R^1$ substituent can be extremely varied.

A particularly preferred $R^4$ substituent of an $SO_2$-linked Ph group is a single-ringed aryl or heteroaryl, phenoxy, thiophenoxy, phenylazo, phenylureido, nicotinamido, isonicotinamido, picolinamido, anilino or benzamido group that is unsubstituted or is itself substituted (optionally substituted) at the para-position when a 6-membered ring or the 3-position when a 5-membered ring. Here, single atoms such as halogen moieties or substituents that contain one to a chain of about ten atoms other than hydrogen such as $C_1$-$C_{10}$ hydrocarbyl, $C_1$-$C_9$ hydrocarbyloxy or carboxyethyl groups can be used.

Exemplary particularly preferred $PhR^4$ (particularly preferred $R^1$) substituents include biphenyl, 4-phenoxyphenyl, 4-thiophenoxyphenyl, 4-benzamidophenyl, 4-phenylureido, 4-anilinophenyl, 4-nicotinamido, 4-isonicotinamido, and 4-picolinamido. Exemplary particularly preferred $R^4$ groups contain a 6-membered aromatic ring and include a phenyl group, a phenoxy group, a thiophenoxy group, a phenylazo group, a phenylureido group, an anilino group, a nicotinamido group, an isonicotinamido group, a picolinamido group and a benzamido group.

More specifically, a particularly preferred sulfonyl butanhydroxamate compounds has an $R^4$ substituent that is a phenyl group, a phenoxy group, a thiophenoxy group, a phenylazo group, a phenylureido group, an anilino group, a nicotinamido group, an isonicotinamido group, a picolinamido group or a benzamido group that is itself optionally substituted at its own meta or para-position or both with a moiety that is selected from the group consisting of a halogen, a $C_1$-$C_9$ hydrocarbyloxy (—O—$C_1$-$C_9$ hydrocarbyl) group, a $C_1$-$C_{10}$ hydrocarbyl group, a di-$C_1$-$C_9$ hydrocarbylamino [—N($C_1$-$C_9$ hydrocarbyl)($C_1$-$C_9$ hydrocarbyl)] group, a carboxyl $C_1$-$C_8$ hydrocarbyl ($C_1$-$C_8$ hydrocarbyl-$CO_2H$) group, a $C_1$-$C_4$ hydrocarbyloxy carbonyl $C_1$-$C_4$ hydrocarbyl [$C_1$-$C_4$ hydrocarbyl-O—(CO)—$C_1$-$C_4$ hydrocarbyl] group, a $C_1$-$C_4$ hydrocarbyloxycarbonyl $C_1$-$C_4$ hydrocarbyl [$C_1$-$C_4$ hydrocarbyl (CO)—O—$C_1$-$C_4$ hydrocarbyl] group and a $C_1$-$C_8$ hydrocarbyl carboxamido [—NH(CO)—$C_1$-$C_8$ hydrocarbyl] group, or is substituted at the meta- and para-positions by two methyl groups or by a $C_1$-$C_2$ alkylenedioxy group such as a methylenedioxy group.

Inasmuch as a contemplated $SO_2$-linked cyclohydrocarbyl, heterocyclo, aryl or heteroaryl radical is itself preferably substituted with a 6-membered aromatic ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked cyclohydrocarbyl, heterocyclo, aryl or heteroaryl radical. When a $R^4$ substituent is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked cyclohydrocarbyl, heterocyclo, aryl or heteroaryl radical is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

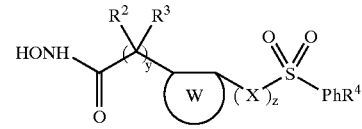

IA

In preferred embodiments, a contemplated compound corresponds in structure to Formula IA, wherein W, X, y, z, $R^2$ and $R^3$ are as defined above, Ph is phenyl substituted at the 4-position with substituent $R^4$ that is defined hereinabove.

$R^2$ and $R^3$ substituents are independently selected. Those groups can be hydrido, $C_1$-$C_4$ hydrocarbyl such as methyl, ethyl, propyl, allyl, propargyl, butyl and but-2-ynyl and the like, hydroxyl or amino.

In addition, $R^2$ and $R^3$ together with the depicted carbon atom to which they are bonded can form a 6-membered heterocyclic ring in which the heteroatom is oxygen, sulfur or nitrogen. That heteroatom is optionally substituted with one or two oxygens when sulfur, and when nitrogen is optionally substituted with a moiety ($R^5$) selected from the group consisting of a $C_1$–$C_4$ hydrocarbyl (as above), $C_3$–$C_6$ cyclohydrocarbyl such as cyclopropyl, cyclobutyl, cyclopentenyl and cyclohexenyl, $C_1$–$C_4$ acylhydrocarbyl such as formyl, acetyl, acrylyol, and butyryl, and a sulfonyl $C_1$–$C_4$ hydrocarbyl group such as methylsulfonyl, ethylsulfonyl and the like. Thus, $R^2$ and $R^3$ together can form a 4-tetrahydrothiopyranyl group, its corresponding sulfoxide or sulfone, a 4-piperidinyl or a 4-tetrahydropyranyl group. When present, the 4-piperidinyl group can be N-substituted with an above-described $R^5$ substituent.

The length of a $R^1$ substituent bonded to the $SO_2$ group is believed to play a role in the overall activity of a contemplated inhibitor compound against MMP enzymes generally. Thus, a compound having an $R^1$ substituent that is shorter in length than a heptyl group, e.g., a 4-methoxyphenyl group (compound of Example 6), typically exhibits moderate to poor inhibitory activity against all of the MMP enzymes, whereas compounds whose $R^1$ substituents have a length of about an heptyl chain or longer, e.g., a 4-phenoxyphenyl group (compound of Example 1) that has a length of about a nine-carbon chain, typically exhibit good to excellent potencies against MMP-13 or MMP-2 and also selectivity against MMP-1. Exemplary data are provided in Table 32 hereinafter in which the activities of the above two compounds can be compared.

The data of Table 32 also illustrate that compounds of seemingly similar structure are not particularly effective inhibitors of the activity of MMP-13. Thus, those data indicate that the before-noted spacing of three carbon atoms between the carbonyl of the hydroxamate and the sulfonyl group has some criticality for these compounds and that the third carbon cannot be replaced by an amido nitrogen atom.

In view of the above-discussed preferences, compounds corresponding in structure to particular formulas constitute particularly preferred embodiments.

In one of those embodiments, a contemplated compound corresponds in structure to Formula II, below,

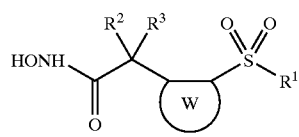

II wherein W, $R^1$, $R^2$, and $R^3$ are as defined above, and $R^1$ is preferably $PhR^4$, as is also defined above.

In another of those embodiments, a contemplated compound corresponds in structure to Formula III, below,

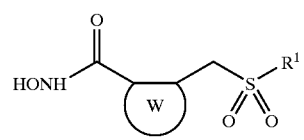

III wherein W, $R^1$, $R^2$, and $R^3$ are as defined above, and $R^1$ is preferably $PhR^4$, as is also defined above.

Taking into account the before-stated preference that W be a 1,2-phenylene radical and the preference for $R^1$ being $PhR^4$, particularly preferred compounds of Formulas II and III correspond in structure to Formulas IIA and IIIA, below,

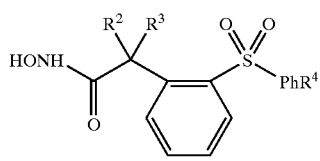

IIA

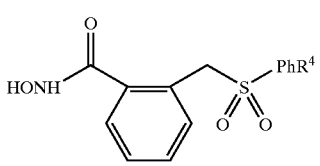

IIIA wherein the above definitions for $R^2$, $R^3$ and $PhR^4$ also apply.

In yet another group of preferred compounds, $R^2$ and $R^3$ together with the carbon atom to which they are bonded form a 4-piperidinyl or tetrahydropyranyl group in which the nitrogen of the 4-piperidinyl group is optionally substituted with a moiety $R^5$ selected from the group consisting of a $C_1$–$C_4$ hydrocarbyl, $C_3$–$C_6$ cyclohydrocarbyl, $C_1$–$C_4$ acylhydrocarbyl, and a sulfonyl $C_1$–$C_4$ hydrocarbyl group. Those preferred compounds correspond in structure to Formulas V and IV, respectively,

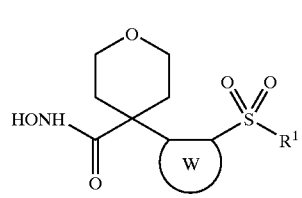

IV

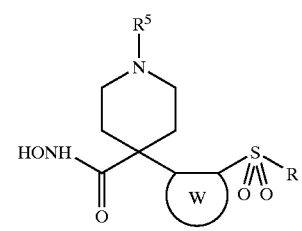

V wherein $R^1$ is as defined above, and is preferably $PhR^4$, as is also defined above.

Again taking into account the before-stated preference that W be a 1,2-phenylene radical and the preference for $R^1$ being $PhR^4$, particularly preferred compounds of Formulas IV and V correspond in structure to Formulas IVA and VA, below, wherein the above definitions for $R^5$ and $PhR^4$ also apply.

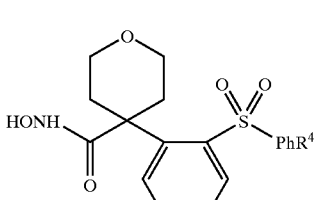

IVA

-continued

VA

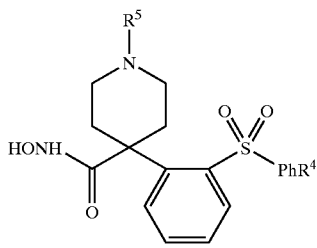

The word "hydrocarbyl" is used herein as a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., $C_1$–$C_4$ alkyl, methyl or dodecenyl. Exemplary hydrocarbyl groups contain a chain of 1 to about 12 carbon atoms, and preferably one to about 10 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a —C(O)O— functionality is referred to as a hydrocarboyl group inasmuch as there is no ambiguity in using that suffix. As a skilled worker will understand, a substituent that cannot exist such as a $C_1$ alkenyl group is not intended to be encompassed by the word "hydrocarbyl".

The term "carbonyl", alone or in combination, means a —C(═O)— group wherein the remaining two bonds (valences) are independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —NH$_2$ group, whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—N$^+$(substituent)$_4$) that is positively charged and accompanied by a counter ion or N-oxide means one substituent is oxygen and the group is represented as (—N$^+$(substituent)$_3$-O$^-$); i.e., the charges are internally compensated.

The term "cyano", alone or in combination, means a —C-triple bond-N (—CN) group. The term "azido", alone or in combination, means an —N-double bond-N-double bond-N— (—N═N═N—).

The term "hydroxyl", alone or in combination, means a —OH group. The term "nitro", alone or in combination, means a —NO$_2$ group.

The term "azo", alone or in combination, means a —N═N— group wherein the bonds at the terminal positions are independently substituted. The term "hydrazino", alone or in combination, means a —NH—NH— group wherein the remaining two bonds (valences) are independently substituted. The hydrogen atoms of the hydrazino group can be replaced, independently, with substituents and the nitrogen atoms can form acid addition salts or be quaternized.

The term "sulfonyl", alone or in combination, means a —S(O)$_2$— group wherein the remaining two bonds (valences) can be independently substituted. The term "sulfoxido", alone or in combination, means a —S(═O)$_1$— group wherein the remaining two bonds (valences) can be independently substituted. The term "sulfonylamide", alone or in combination, means a —S(═O)$_2$—N═ group wherein the remaining three bonds (valences) are independently substituted. The term "sulfinamido", alone or in combination, means a —S(═O)$_1$N═ group wherein the remaining three bonds (valences) are independently substituted. The term "sulfenamide", alone or in combination, means a —S—N═ group wherein the remaining three bonds (valences) are independently substituted.

The term "hydrocarbyloxyl", alone or in combination, means an hydrocarbyl ether radical wherein the term hydrocarbyl is as defined above. Examples of suitable hydrocarbyl ether radicals include methoxy, ethoxy, n-propoxy, isopropoxy, allyloxy, n-butoxy, iso-butoxy, sec-butoxy, tert-butoxy and the like. The term "cyclohydrocarbyl", alone or in combination, means a hydrocarbyl radical that contains 3 to about 8 carbon atoms, preferably from about 3 to about 6 carbon atoms, and is cyclic. The term "cyclohydrocarbyl-hydrocarbyl" means an hydrocarbyl radical as defined above which is substituted by a cyclohydrocarbyl as also defined above. Examples of such cyclohydrocarbylhydrocarbyl radicals include cyclopropyl, cyclobutyl, cyclopentenyl, cyclohexyl cyclooctynyl and the like.

The term "aryl", alone or in combination, means a phenyl or naphthyl radical that optionally carries one or more substituents selected from hydrocarbyl, hydrocarbyloxy, halogen, hydroxy, amino, nitro and the like, such ads phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means an hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

The terms "hydrocarbyloyl" or "hydrocarbylcarbonyl", alone or in combination, mean an acyl radical derived from an hydrocarbylcarboxylic acid, examples of which include acetyl, propionyl, acryloyl, butyryl, valeryl, 4-methylvaleryl, and the like. The term "cyclohydrocarbylcarbonyl" means an acyl group derived from a monocyclic or bridged cyclohydrocarbylcarboxylic acid such as cyclopropanecarbonyl, cyclohexenecarbonyl, adamantanecarbonyl, and the like, or from a benz-fused monocyclic cyclohydrocarbylcarboxylic acid that is optionally substituted by, for example, a hydrocarbyloylamino group, such as 1,2,3,4-tetrahydro-2-naphthoyl, 2-acetamido-1,2,3,4-tetrahydro-2-naphthoyl. The terms "arylhydrocarbyloyl" or "arylhydrocarbylcarbony" mean an acyl radical derived from an aryl-substituted hydrocarbylcarboxylic acid such as phenylacetyl, 3-phenylpropenyl (cinnamoyl), 4-phenylbutyryl, (2-naphthyl)acetyl, 4-chlorohydrocinnamoyl, 4-aminocinnamoyl, 4-methoxycinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocyclohydrocarbyl portion of a heterocyclylcarbonyl, heterocyclyloxycarbonyl, heterocyclylhydrocarbyloxycarbonyl, or heterocyclohydrocarbyl group or the like is a saturated or partially unsaturated monocyclic, bicyclic or tricyclic heterocycle that contains one to four hetero atoms selected from nitrogen, oxygen and sulphur, which is optionally substituted on one or more carbon atoms by a halogen, alkyl, alkoxy, oxo group, and the like, and/or on a secondary nitrogen atom (i.e., —NH—) by an hydrocarbyl, arylhydrocarbyloxycarbonyl, hydrocarbyloyl, aryl or arylhydrocarbyl or on a tertiary nitrogen atom (i.e. =N—) by oxido and that is attached via a carbon atom. The tertiary nitrogen atom with three substituents can also form a N-oxide [=N(O)—] group. Examples of such heterocyclyl groups are pyrrolidinyl, piperidinyl, piperazinyl, morpholinyl, thiamorpholinyl, and the like.

The heteroaryl portion of a heteroaroyl, heteroaryloxycarbonyl, or a heteroarylhydrocarbyloyl (heteroarylhydrocarbyl carbonyl) group or the like is an aromatic monocyclic, bicyclic, or tricyclic heterocycle that contains the hetero atoms and is optionally substituted as defined above with respect to the definition of heterocyclyl. A "heteroaryl" group is an aromatic heterocyclic ring substituent that can contain one, two, three or four atoms in the ring that are other than carbon. Those heteroatoms can be nitrogen, sulfur or oxygen. A heteroaryl group can contain a single five- or 6-membered ring or a fused ring system that contains two 6-membered rings or a five- and a 6-membered ring. Exemplary heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups ; six/5-membered fused ring substituents such as benzothiofuranyl, isobenzothiofuranyl, benzisoxazolyl, benzoxazolyl, purinyl and anthranilyl groups ; and six/6-membered fused rings such as 1,2-,.1,4-,.2,3- and 2,1-benzopyronyl, quinolinyl, isoquinolinyl, cinnolinyl, quinazolinyl, and 1,4-benzoxazinyl groups.

The term "cyclohydrocarbylhydrocarbyloxycarbonyl" means an acyl-group derived from a cyclohydrocarbylhydrocarbyloxycarboxylic acid of the formula cyclohydrocarbylhydrocarbyl-O—COOH wherein cyclohydrocarbylhydrocarbylhas the significance given above. The term "aryloxyhydrocarbyloyl" means an acyl radical of the formula aryl-O-hydrocarbyloyl wherein aryl and hydrocarbyloyl have the significance given above. The term "heterocyclyloxycarbony" means an acyl group derived from heterocyclyl-O—COOH wherein heterocyclyl is as defined above. The term "heterocyclylhydrocarbyloyl" is an acyl radical derived from a heterocyclyl-substituted hydrocarbylcarboxylic acid wherein heterocyclyl has the significance given above. The term "heterocyclylhydrocarbyloxycarbonyl" means an acyl radical derived from a heterocyclyl-substituted hydrocarbyl-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, hydrocarbyl, aryl, aralkyl, cyclohydrocarbyl, cyclohydrocarbylhydrocarbyl radicals and the like. The term "aminohydrocarbyloyl" means an acyl group derived from an amino-substituted hydrocarbylcarboxylic acid wherein the amino group can be a primary, secondary or tertiary amino group containing substituents independently selected from hydrogen, alkyl, aryl, aralkyl, cyclohydrocarbyl, cyclohydrocarbylhydrocarbyl radicals and the like.

The term "halogen" means fluorine, chlorine, bromine or iodine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1,1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl.

Table 1 through Table 31, below, show several contemplated sulfonyl divalent aryl or heteroaryl hydroxamic acid compounds as structural formulas that illustrate substituent groups. Each group of compounds is illustrated by a generic formula, followed by a series of preferred moieties or groups that constitute various substituents that can be attached at the position clearly shown in the generic structure. The substituent symbols, e.g., $R^1$, $R^2$ X, are as shown in each Table, and are different from those shown elsewhere herein in structural formulas bearing Roman numerals. One or two bonds (straight lines) are shown with those substituents to indicate the respective positions of attachment in the illustrated compound. This system is well known in the chemical communication arts and is widely used in scientific papers and presentations.

TABLE 1
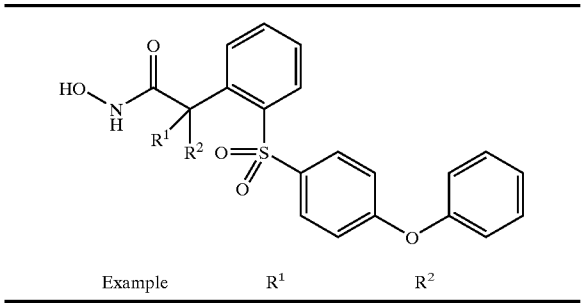
| Example | R¹ | R² |
|---|---|---|
| 1 | —H | —H |
| 2 | —H | —CH₃ |
| 3 | —CH₃ | —CH₃ |
| 4 | —H | —OH |
| 5 | —CH₃ | —OH |
| 6 | |  |
| 7 | |  |
| 8 | |  |
| 9 | |  |
| 10 | |  |
| 11 | |  |
| 12 | |  |
| 13 | |  |
TABLE 1-continued
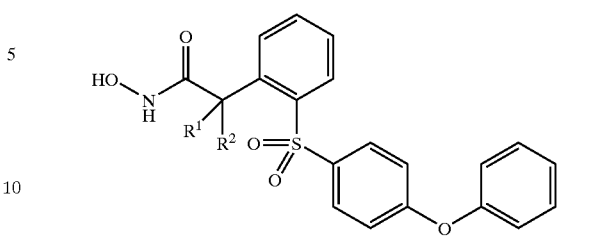
| Example | R¹ R² |
|---|---|
| 14 | |
| 15 | |
| 16 | |
| 17 | |
| 18 | |
| 19 | |

TABLE 1-continued

[Structure: Hydroxamic acid with phenyl group bearing ortho-sulfonyl-(4-phenoxyphenyl) substituent, with R¹ and R² on the α-carbon]

| Example | R¹ | R² |
|---|---|---|
| 20 | | 4,4-disubstituted piperidine N-SO₂CH₃ (spiro from α-carbon, gem-dimethyl) |
| 21 | | 4,4-disubstituted piperidine with N-CH₂C(O)NH₂ |
| 22 | | 4,4-disubstituted piperidine with N-CH₂C(O)OCH₃ |
| 23 | | 4,4-disubstituted piperidine with N-CH₂C(O)NHCH₃ |
| 24 | | 4,4-disubstituted piperidine with N-CH₂C(O)OH |

TABLE 2

[Structure: Hydroxamic acid with pyridyl group bearing sulfonyl-(4-phenoxyphenyl) substituent, with R¹ and R² on the α-carbon]

| Example | R¹ | R² |
|---|---|---|
| 1 | —H | —H |
| 2 | —H | —CH₃ |
| 3 | —CH₃ | —CH₃ |
| 4 | —H | —OH |
| 5 | —CH₃ | —OH |
| 6 | | cyclopropyl (spiro, gem-dimethyl) |
| 7 | | cyclobutyl (spiro, gem-dimethyl) |
| 8 | | cyclopentyl (spiro, gem-dimethyl) |
| 9 | | tetrahydropyran (spiro, gem-dimethyl) |
| 10 | | tetrahydrothiopyran (spiro, gem-dimethyl) |
| 11 | | 4,4-disubstituted piperidine N-H |
| 12 | | 4,4-disubstituted piperidine N-CH₃ |
| 13 | | tetrahydrothiopyran S-oxide (spiro, gem-dimethyl) |

TABLE 2-continued
| Example | R¹ | R² |
|---------|----|----|
| 14 | | 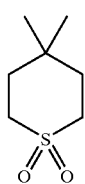 |
| 15 | | 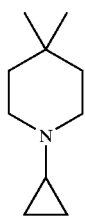 |
| 16 | | 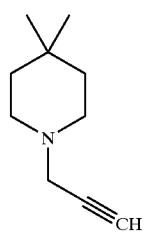 |
| 17 | | 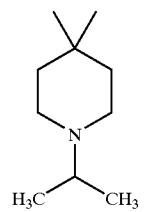 |
| 18 | | 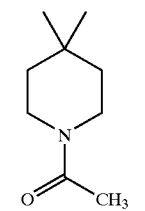 |
| 19 | | 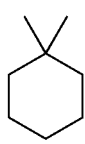 |
TABLE 2-continued
| Example | R¹ | R² |
|---------|----|----|
| 20 | | 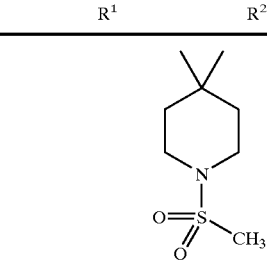 |
| 21 | | 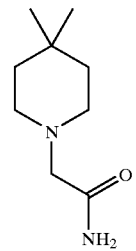 |
| 22 | | 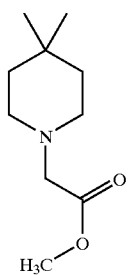 |
| 23 | | 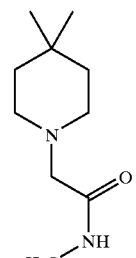 |
| 24 | | 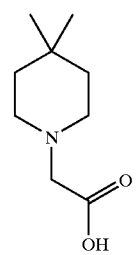 |

TABLE 3

[Structure: hydroxamic acid with R1, R2 substituents on carbon alpha to amide, attached to ortho-substituted phenyl bearing a sulfonyl group linked to para-X-Ar phenyl]

| Example | R¹, R² | X | Ar |
|---|---|---|---|
| 1 | gem-dimethyl cyclopropane | O | 4-pyridyl |
| 2 | gem-dimethyl cyclopropane | O | 3-pyridyl |
| 3 | gem-dimethyl cyclobutane | O | 4-pyridyl |
| 4 | gem-dimethyl cyclobutane | O | 3-pyridyl |
| 5 | gem-dimethyl cyclopentane | O | 4-pyridyl |
| 6 | gem-dimethyl cyclopentane | O | 3-pyridyl |
| 7 | gem-dimethyl cyclohexane | O | 4-pyridyl |
| 8 | gem-dimethyl cyclohexane | O | 3-pyridyl |
| 9 | gem-dimethyl cyclohexane | S | phenyl |
| 10 | gem-dimethyl cyclohexane | S | 4-chlorophenyl |

TABLE 4

[Structure: hydroxamic acid with piperidine spiro center bearing N-propargyl group, attached to ortho-phenyl-sulfonyl-phenyl-X-Ar]

| Example | X | Ar |
|---|---|---|
| 1 | O | phenyl |
| 2 | O | 4-chlorophenyl |
| 3 | O | 3-chlorophenyl |
| 4 | O | 3,4-dichlorophenyl |
| 5 | O | 4-methylphenyl |
| 6 | O | 3-methylphenyl |
| 7 | O | 3,4-dimethylphenyl |
| 8 | O | 3-pyridyl |
| 9 | O | 4-pyridyl |
| 10 | O | 4-fluorophenyl |

TABLE 4-continued
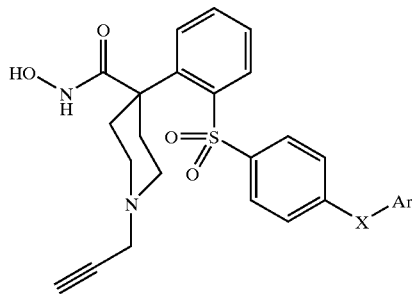
| Example | X | Ar |
|---|---|---|
| 11 | O | 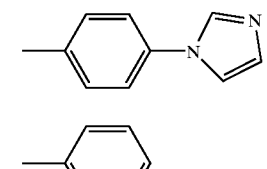 |
| 12 | S | 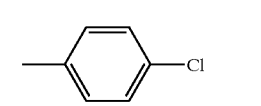 |
| 13 | S | 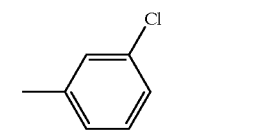 |
| 14 | S | 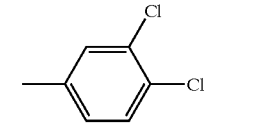 |
| 15 | S | 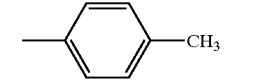 |
| 16 | S | 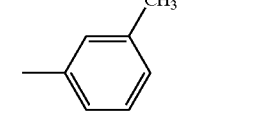 |
| 17 | S | 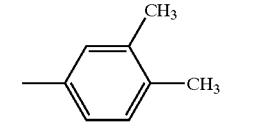 |
| 18 | S | 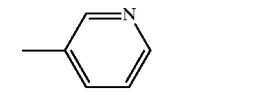 |
| 19 | S | 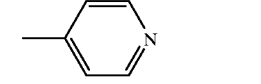 |
| 20 | S | 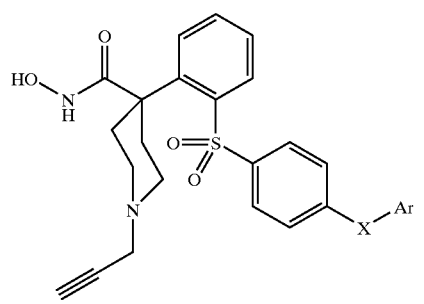 |
TABLE 4-continued
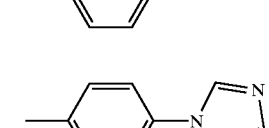
| Example | X | Ar |
|---|---|---|
| 21 | S |  |
| 22 | S | 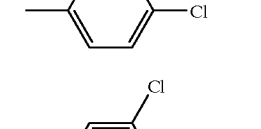 |
TABLE 5
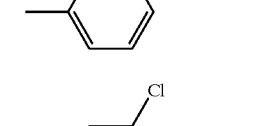
| Example | X | Ar |
|---|---|---|
| 1 | O | 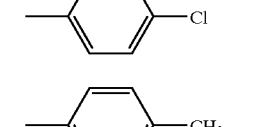 |
| 2 | O | 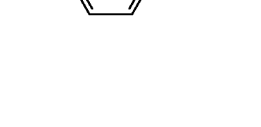 |
| 3 | O | |
| 4 | O | |
| 5 | O | |

TABLE 5-continued

[Structure: hydroxamic acid with tetrahydropyran, phenyl, and sulfonyl-phenyl-X-Ar groups]

| Example | X | Ar |
|---------|---|-----|
| 6 | O | 3,4-dimethylphenyl (CH₃ at 3 and 4 positions... actually 2,4-dimethyl per image: CH₃) — 2-methyl with additional CH₃ |
| 7 | O | dimethylphenyl (two CH₃) |
| 8 | O | pyridin-3-yl |
| 9 | O | pyridin-4-yl |
| 10 | O | 4-fluorophenyl |
| 11 | O | 4-(1-imidazolyl)phenyl |
| 12 | S | phenyl |
| 13 | S | 4-chlorophenyl |
| 14 | S | 3-chlorophenyl |
| 15 | S | 3,4-dichlorophenyl |
| 16 | S | 4-methylphenyl |
| 17 | S | 3-methylphenyl (dimethyl) |
| 18 | S | dimethylphenyl |
| 19 | S | pyridin-3-yl |
| 20 | S | pyridin-4-yl |
| 21 | S | 4-fluorophenyl |
| 22 | S | 4-(1-imidazolyl)phenyl |

TABLE 6

[Structure: hydroxamic acid with tetrahydropyran, phenyl, and sulfonyl-phenyl-X-Ar groups]

| Example | X | Ar |
|---------|---|-----|
| 1 | O | 4-(1,2,4-triazol-1-yl)phenyl |
| 2 | O | 4-(1,2,4-triazol-1-yl)phenyl |

TABLE 6-continued
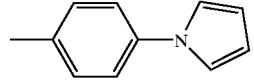
| Example | X | Ar |
|---|---|---|
| 3 | O | 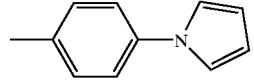 |
| 4 | O | 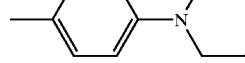 |
| 5 | O | 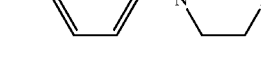 |
| 6 | O | 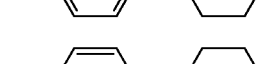 |
| 7 | O | 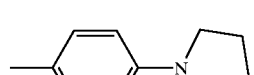 |
| 8 | O | 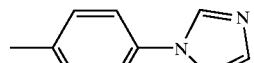 |
| 9 | S | 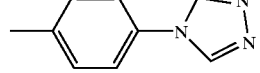 |
| 10 | S | 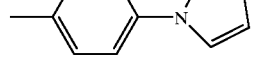 |
| 11 | S | 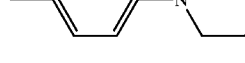 |
| 12 | S | 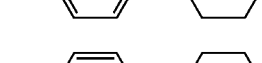 |
| 13 | S | 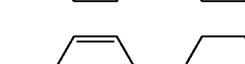 |
| 14 | S |  |
| 15 | S |  |
TABLE 6-continued
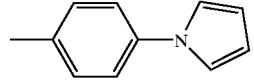
| Example | X | Ar |
|---|---|---|
| 16 | S | 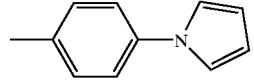 |
TABLE 7
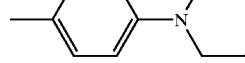
| Example | X |
|---|---|
| 1 | 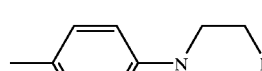 |
| 2 | 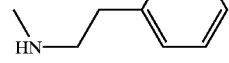 |
| 3 | 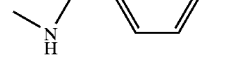 |
| 4 | 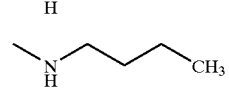 |
| 5 | 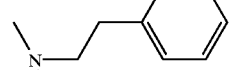 |
| 6 | 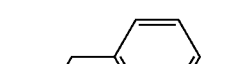 |
| 7 |  |

TABLE 7-continued

[Structure: hydroxamic acid compound with tetrahydropyran core, phenyl-sulfonyl-phenyl-X substituent]

| Example | X |
|---|---|
| 8 | -N(CH₃)-CH₂CH₂CH₂CH₃ with N-CH₃ |
| 9 | -NH-CH₂CH₂-(4-pyridyl) |
| 10 | -NH-CH₂-(4-pyridyl) |
| 11 | -NH-CH₂CH₂-(3-pyridyl) |
| 12 | -NH-CH₂-(3-pyridyl) |
| 13 | -N(CH₃)-CH₂CH₂-(3-pyridyl) with N-CH₃ |
| 14 | -N(CH₃)-CH₂-(3-pyridyl) with N-CH₃ |
| 15 | -NH-CH₂CH₂-(4-methoxyphenyl) |
| 16 | -NH-CH₂-(4-methoxyphenyl) |
| 17 | -NH-CH₂CH₂-(4-chlorophenyl) |
| 18 | -NH-CH₂-(4-chlorophenyl) |

TABLE 7-continued

[Same core structure]

| Example | X |
|---|---|
| 19 | -NH-CH₂CH₂-(4-methylphenyl) |
| 20 | -NH-CH₂-(4-methylphenyl) |

TABLE 8

[Structure: hydroxamic acid compound with piperidine core bearing N-propargyl group, phenyl-sulfonyl-phenyl-X substituent]

| Example | X |
|---|---|
| 1 | -NH-CH₂CH₂-phenyl |
| 2 | -NH-CH₂-phenyl |
| 3 | -NH-CH₂CH₂-CH₃ |
| 4 | -NH-CH₂CH₂CH₂-CH₃ |
| 5 | -N(CH₃)-CH₂CH₂-phenyl |

TABLE 8-continued

| Example | X |
|---|---|
| 6 | N,N-dimethyl benzylamine |
| 7 | N,N-dimethyl propylamine |
| 8 | N,N-dimethyl butylamine |
| 9 | N-methyl 2-(pyridin-4-yl)ethylamine |
| 10 | N-methyl (pyridin-4-yl)methylamine |
| 11 | N-methyl 2-(pyridin-3-yl)ethylamine |
| 12 | N-methyl (pyridin-3-yl)methylamine |
| 13 | N,N-dimethyl 2-(pyridin-3-yl)ethylamine |
| 14 | N,N-dimethyl (pyridin-3-yl)methylamine |
| 15 | N-methyl 2-(4-methoxyphenyl)ethylamine |
| 16 | N-methyl (4-methoxyphenyl)methylamine |
| 17 | N-methyl 2-(4-chlorophenyl)ethylamine |
| 18 | N-methyl (4-chlorophenyl)methylamine |
| 19 | N-methyl 2-(4-methylphenyl)ethylamine |
| 20 | N-methyl (4-methylphenyl)methylamine |

TABLE 9

| Example | X |
|---|---|
| 1 | 1-methyl-4-phenylpiperidine |
| 2 | 1-methyl-3-methylpiperidine |

TABLE 9-continued

[Structure: Core scaffold with hydroxamic acid (HO-NH-C(=O)-), quaternary carbon bearing a 2-substituted phenyl group, piperidine ring with N-propargyl substituent, and arylsulfonyl group (SO₂-C₆H₄-X) on the phenyl ring]

| Example | X |
|---|---|
| 3 | N-methylpiperidine with 4-OH and 4-phenyl substituents |
| 4 | N-methylpiperidine-4-carboxylic acid ethyl ester |
| 5 | N-methylpiperidine-4-carboxamide |
| 6 | N-methylpiperidine-3-carboxamide |
| 7 | N-methyl-1,4-dioxa-8-azaspiro[4.5]decane |
| 8 | N-morpholinyl |
| 9 | N-methyl-3,5-dimethylpiperidine |
| 10 | N-methylpiperazine (NH) |
| 11 | 4-phenyl-N-methylpiperazine |
| 12 | 4-(4-acetylphenyl)-N-methylpiperazine |

TABLE 9-continued

[Same core structure as above]

| Example | X |
|---|---|
| 13 | 4-(3-trifluoromethylphenyl)-N-methylpiperazine |
| 14 | 4-(4-fluorophenyl)-N-methylpiperazine |
| 15 | 4-(4-nitrophenyl)-N-methylpiperazine |
| 16 | 4-(3-fluorophenyl)-N-methylpiperazine |

TABLE 10

[Structure: Core scaffold with hydroxamic acid (HO-NH-C(=O)-), quaternary carbon bearing a 2-substituted phenyl group, tetrahydropyran ring (oxygen-containing), and arylsulfonyl group (SO₂-C₆H₄-X)]

| Example | X |
|---|---|
| 1 | 4-phenyl-N-methylpiperidine |
| 2 | 3-methyl-N-methylpiperidine |
| 3 | 4-hydroxy-4-phenyl-N-methylpiperidine |

TABLE 10-continued
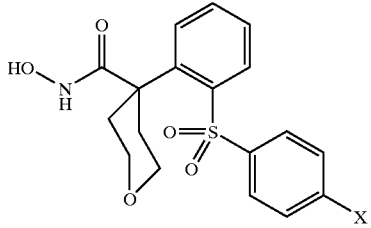
| Example | X |
|---|---|
| 4 | 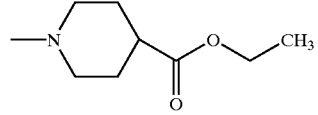 |
| 5 | 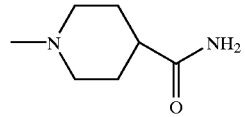 |
| 6 | 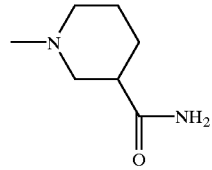 |
| 7 |  |
| 8 | 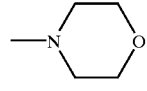 |
| 9 | 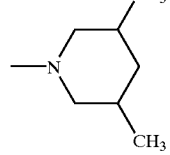 |
| 10 | 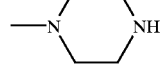 |
| 11 | 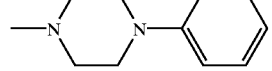 |
| 12 | 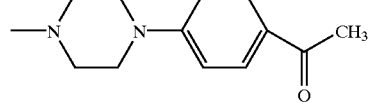 |
| 13 | 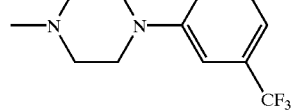 |
| 14 | 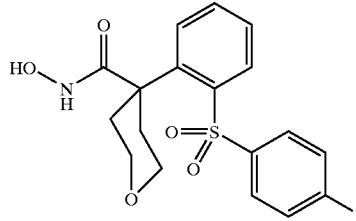 |
| 15 | 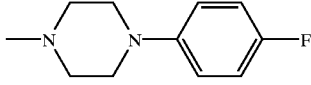 |
| 16 | 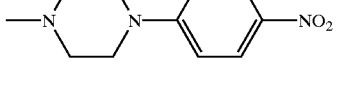 |
TABLE 11
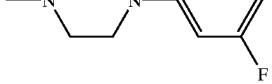
| Example | X |
|---|---|
| 1 | 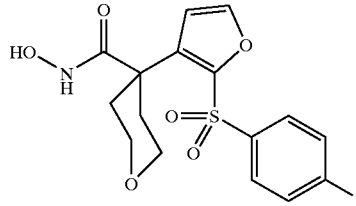 |
| 2 | 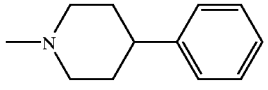 |
| 3 | 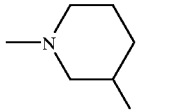 |
| 4 | 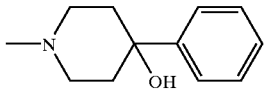 |
| 5 | 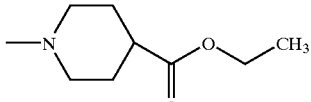 |

TABLE 11-continued

[Structure: hydroxamic acid furan sulfonyl phenyl compound with X substituent]

| Example | X |
|---------|---|
| 6 | 1-methylpiperidine-3-carboxamide |
| 7 | 1,4-dioxa-8-azaspiro[4.5]decane (N-methyl) |
| 8 | 4-methylmorpholine |
| 9 | 1,3,5-trimethylpiperidine (3,5-dimethyl-1-methylpiperidine) |
| 10 | 4-methylpiperazine (N-methyl, NH) |
| 11 | 1-methyl-4-phenylpiperazine |
| 12 | 1-methyl-4-(4-acetylphenyl)piperazine |
| 13 | 1-methyl-4-(3-trifluoromethylphenyl)piperazine |
| 14 | 1-methyl-4-(4-fluorophenyl)piperazine |
| 15 | 1-methyl-4-(4-nitrophenyl)piperazine |

TABLE 11-continued

[Structure: hydroxamic acid furan sulfonyl phenyl compound with X substituent]

| Example | X |
|---------|---|
| 16 | 1-methyl-4-(3-fluorophenyl)piperazine |

TABLE 12

[Structure: hydroxamic acid furan sulfonyl phenyl compound with X substituent]

| Example | X |
|---------|---|
| 1 | 1-methylpiperidine-4-carboxylic acid ethylamide |
| 2 | 1-methylpiperidine-3-carboxylic acid methylamide |
| 3 | 1-methylpiperidine-3-carbonyl morpholine |
| 4 | 1-methylpiperidine-4-carbonyl glycine |
| 5 | 1-methylpiperidine-3-carboxylic acid N,N-dimethylamide |

TABLE 12-continued
| Example | X |
|---|---|
| 6 | 1-methylpiperidin-3-yl-methyl-morpholine |
| 7 | 1-methylpiperidin-3-yl-C(O)CF$_3$ |
| 8 | 1-methylpiperidin-4-yl-O-propyl |
| 9 | 1-methylpiperidin-4-yl-O-CH$_2$CH$_2$-OMe |
| 10 | 1-methylpiperidin-4-yl-O-CH$_2$CH$_2$-Cl |
| 11 | 1-methylpiperidin-4-yl-O-CH$_2$CH$_2$-Ph |
TABLE 13
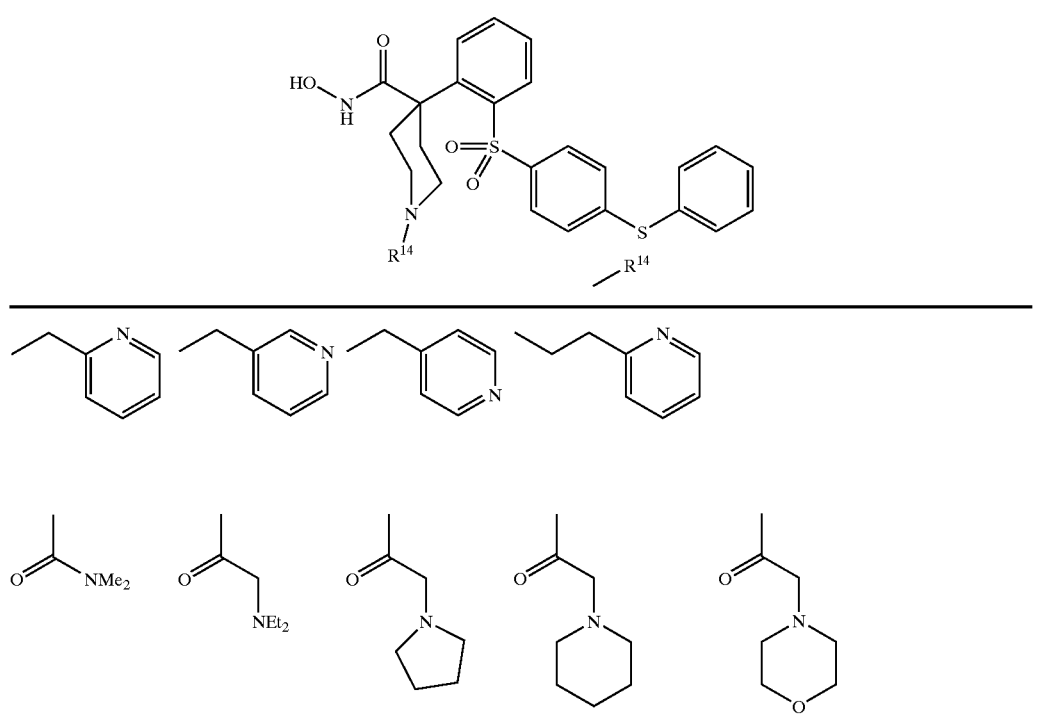

TABLE 13-continued
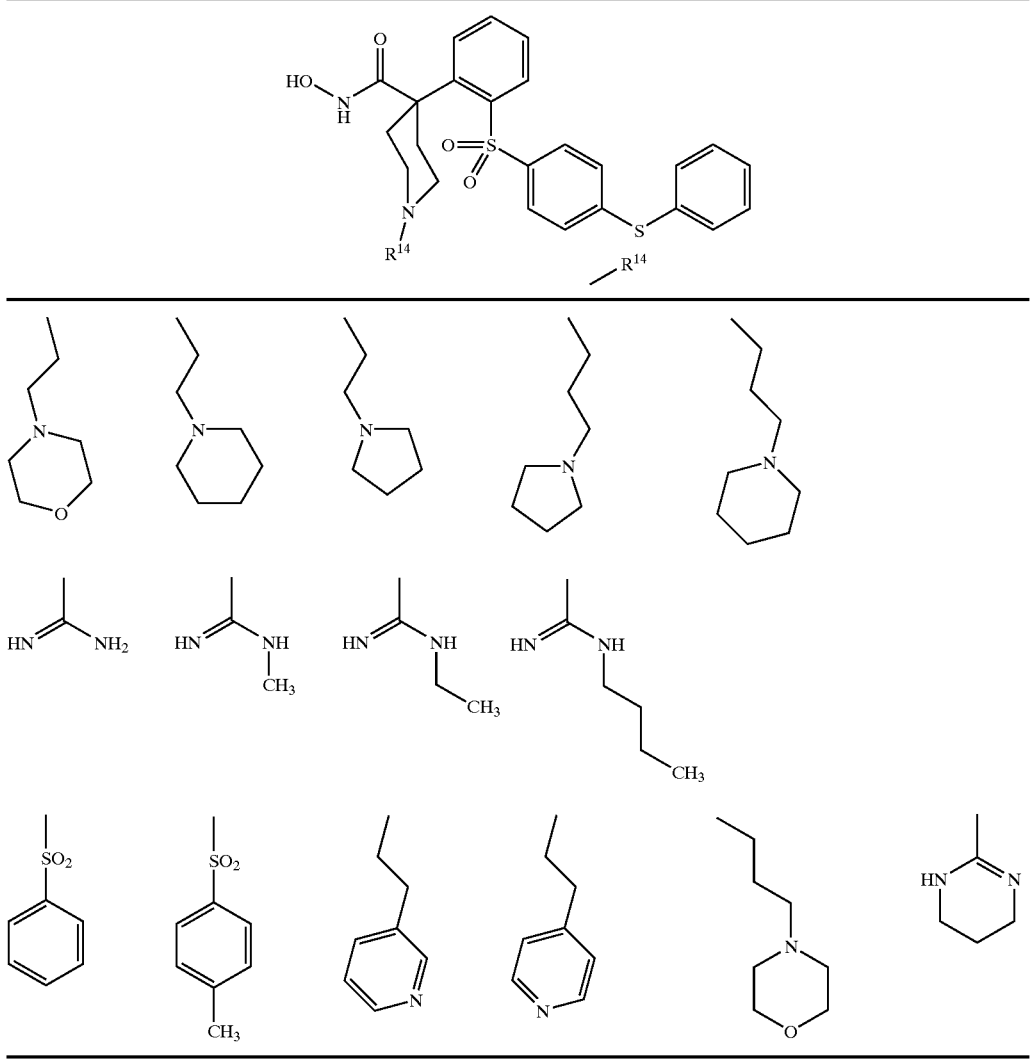
TABLE 14
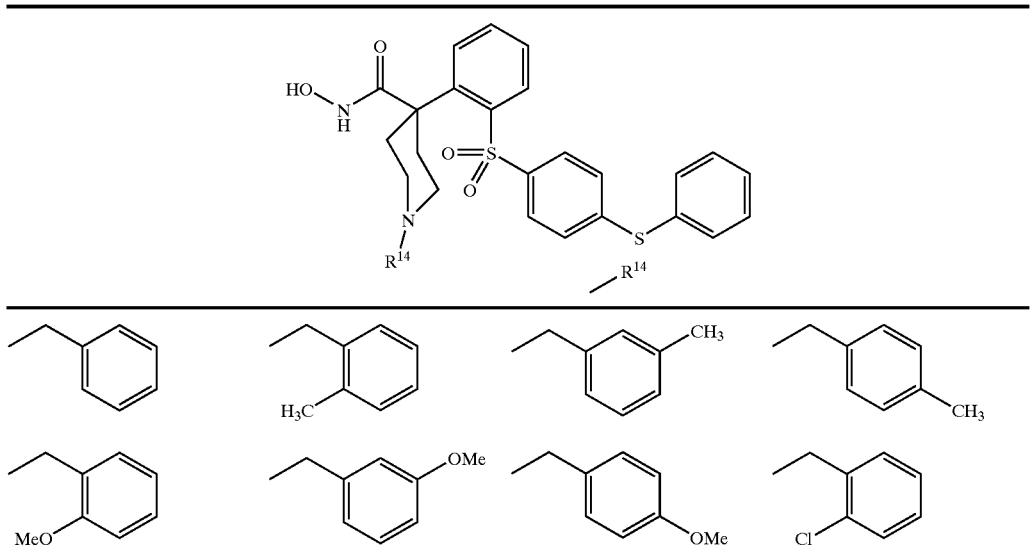

TABLE 14-continued
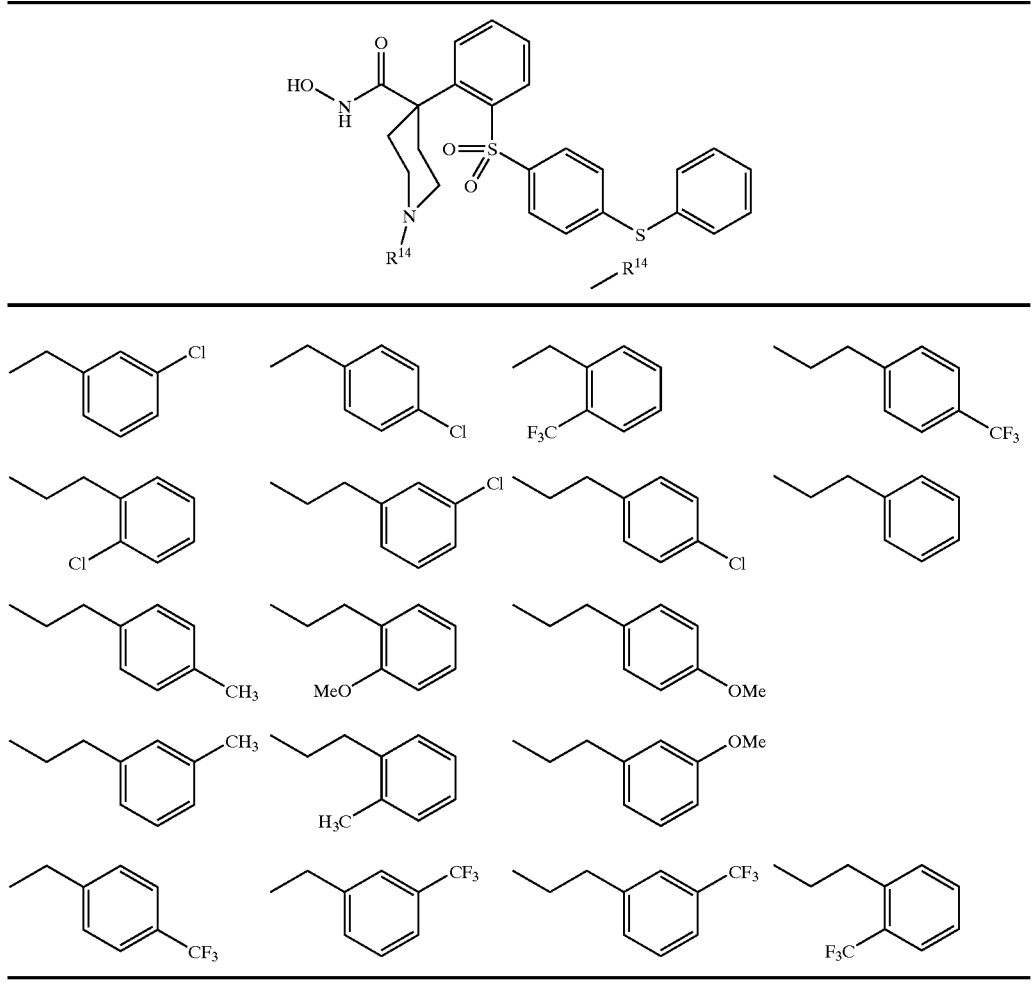
TABLE 15
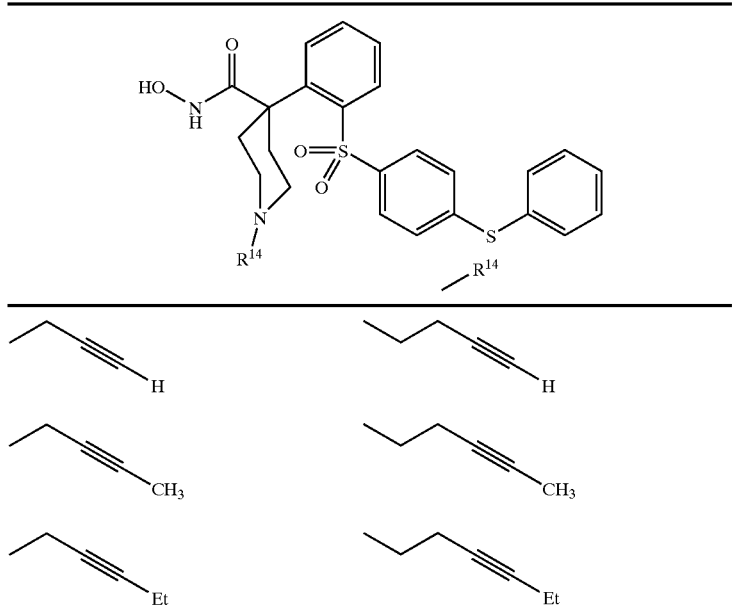

TABLE 15-continued
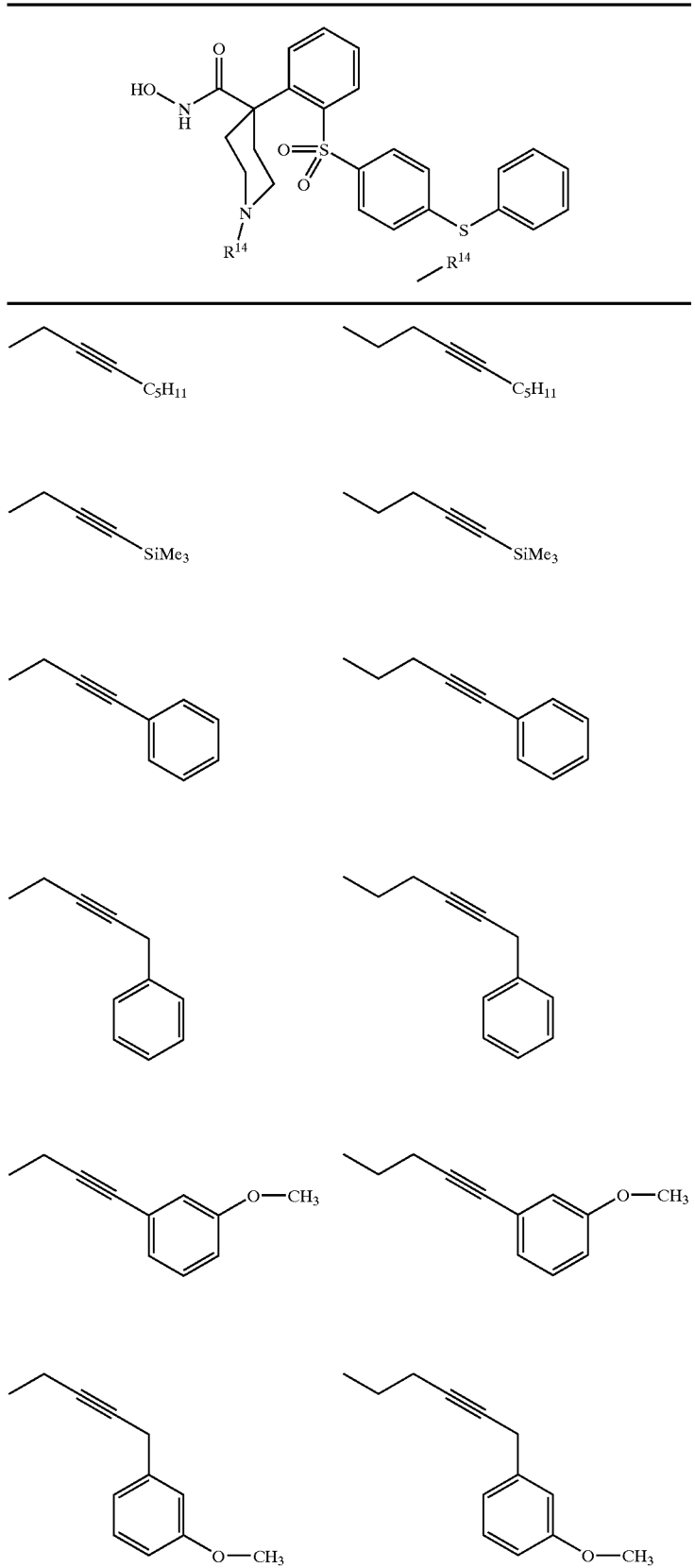

TABLE 15-continued
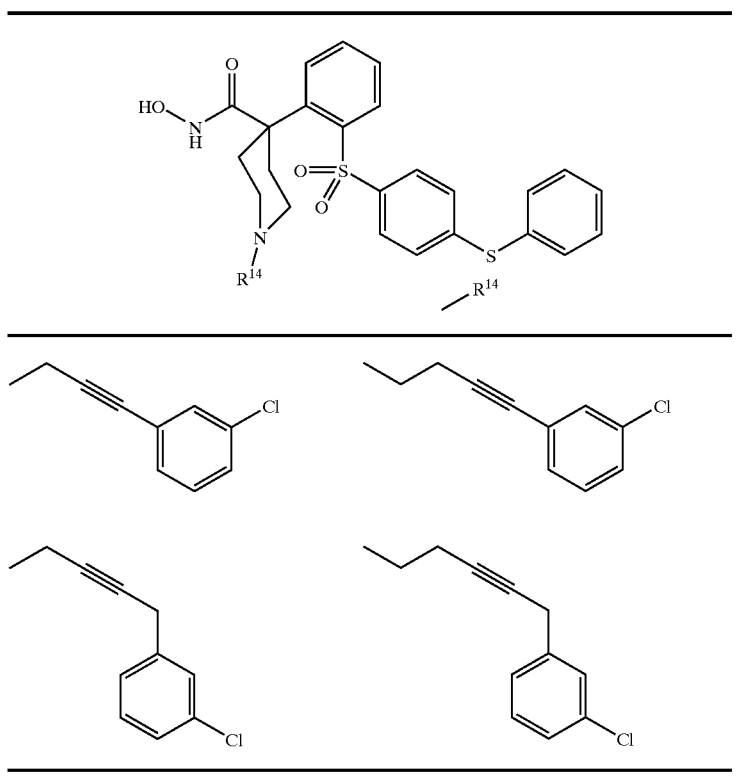
TABLE 16
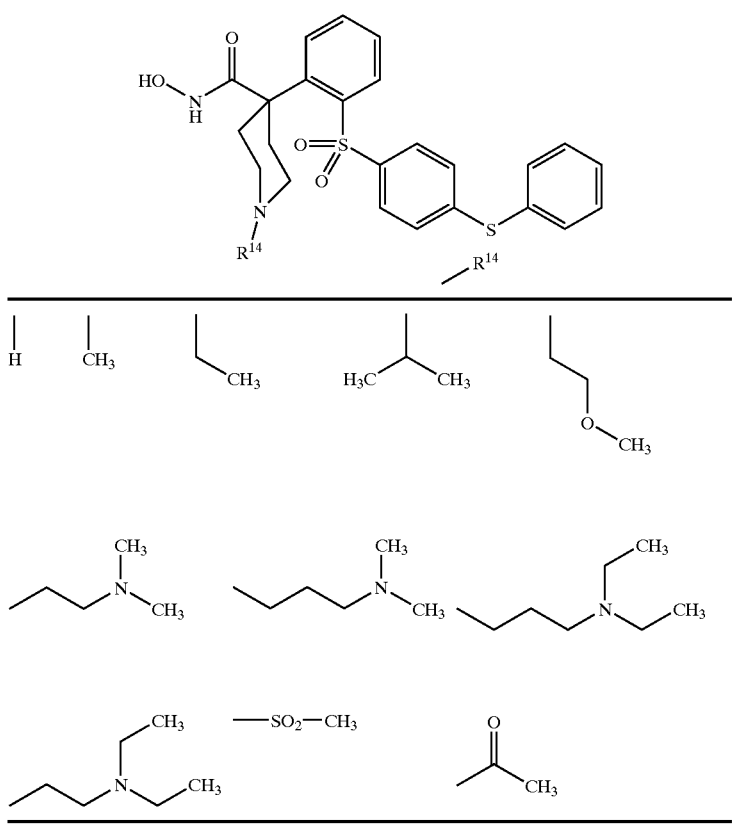

TABLE 17
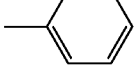
| Example | X | Ar |
|---|---|---|
| 1 | O | 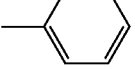 |
| 2 | O | 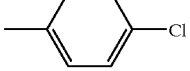 |
| 3 | O |  |
| 4 | O | 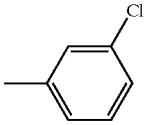 |
| 5 | O | 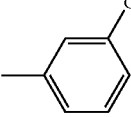 |
| 6 | O | 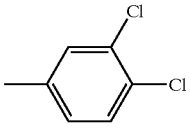 |
| 7 | O | 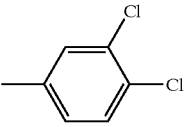 |
| 8 | O | 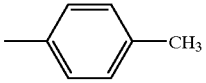 |
| 9 | O | 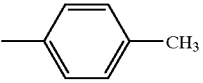 |
| 10 | O | 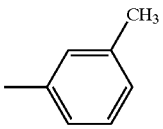 |
| 11 | O | 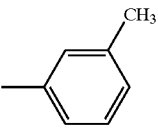 |
TABLE 17-continued
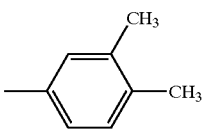
| Example | X | Ar |
|---|---|---|
| 12 | S | 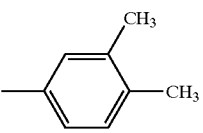 |
| 13 | S | 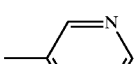 |
| 14 | S | 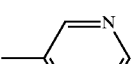 |
| 15 | S | 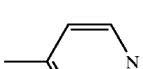 |
| 16 | S | 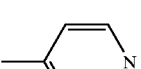 |
| 17 | S | 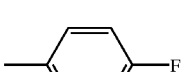 |
| 18 | S | 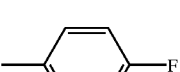 |
| 19 | S | 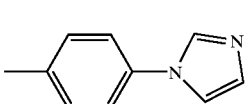 |
| 20 | S | 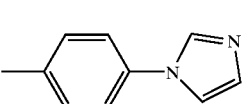 |
| 21 | S |  |
| 22 | S |  |

TABLE 18
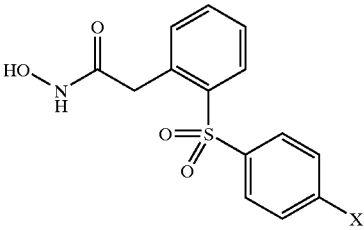
| Example | X |
|---------|---|
| 1 | 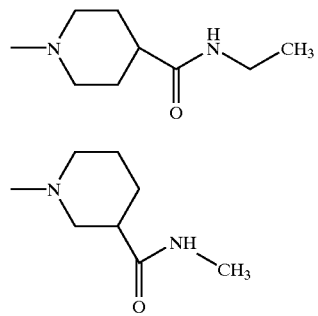 |
| 2 | 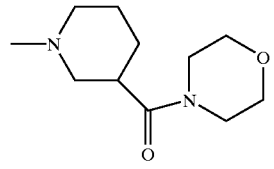 |
| 3 | 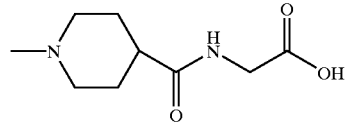 |
| 4 | 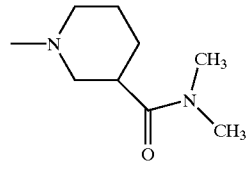 |
| 5 | 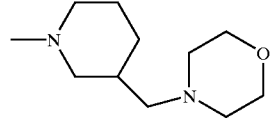 |
| 6 | 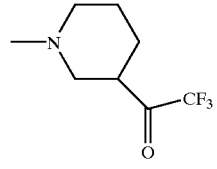 |
| 7 | 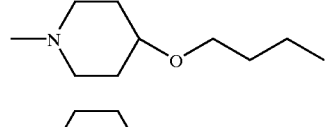 |
| 8 | 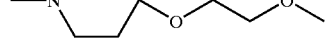 |
| 9 | 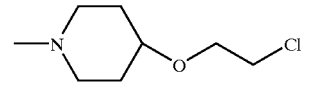 |
TABLE 18-continued
| Example | X |
|---------|---|
| 10 | 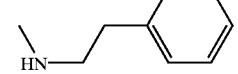 |
| 11 | 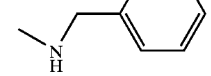 |
TABLE 19
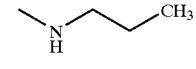
| Example | X |
|---------|---|
| 1 |  |
| 2 | 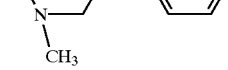 |
| 3 | 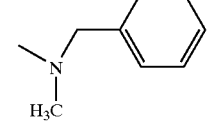 |
| 4 | |
| 5 | |
| 6 | |

TABLE 19-continued

[Structure: 2-(hydroxyamino-oxo-ethyl)phenyl sulfonyl-phenyl-X]

| Example | X |
|---------|---|
| 7 | -N(CH₃)-CH₂CH₂-N(CH₃)(CH₃) — dimethylaminoethyl-methylamino |
| 8 | -N(CH₃)-CH₂CH₂CH₂-N(CH₃)(CH₃) — dimethylaminopropyl-methylamino |
| 9 | -NH-CH₂CH₂-(4-pyridyl) |
| 10 | -NH-CH₂-(4-pyridyl) |
| 11 | -NH-CH₂CH₂-(3-pyridyl) |
| 12 | -NH-CH₂-(3-pyridyl) |
| 13 | -N(CH₃)-CH₂CH₂-(3-pyridyl), with H₃C on N |
| 14 | -N(CH₃)-CH₂-(3-pyridyl), with CH₃ on N |
| 15 | -NH-CH₂CH₂-(4-methoxyphenyl) |
| 16 | -NH-CH₂-(4-methoxyphenyl) |
| 17 | -NH-CH₂CH₂-(4-chlorophenyl) |

TABLE 19-continued

[Structure: 2-(hydroxyamino-oxo-ethyl)phenyl sulfonyl-phenyl-X]

| Example | X |
|---------|---|
| 18 | -NH-CH₂-(4-chlorophenyl) |
| 19 | -NH-CH₂CH₂-(4-methylphenyl) |
| 20 | -NH-CH₂-(4-methylphenyl) |

TABLE 20

[Structure: 2-(hydroxyamino-oxo-ethyl)phenyl sulfonyl-phenyl-X]

| Example | X |
|---------|---|
| 1 | 1-methyl-4-phenyl-piperidinyl |
| 2 | 1-methyl-3-methyl-piperidinyl |
| 3 | 1-methyl-4-hydroxy-4-phenyl-piperidinyl |
| 4 | 1-methyl-piperidine-4-carboxylic acid ethyl ester |

TABLE 20-continued

[Structure: hydroxamic acid with phenyl-sulfonyl-phenyl-X]

| Example | X |
|---------|---|
| 5 | 1-methylpiperidine-4-carboxamide |
| 6 | 1-methylpiperidine-3-carboxamide |
| 7 | 1,4-dioxa-8-azaspiro[4.5]decane (N-linked) |
| 8 | morpholine (N-linked) |
| 9 | 3,5-dimethyl-1-methylpiperidine (N-linked via N1... dimethyl piperidine) |
| 10 | piperazine (N-linked, NH) |
| 11 | 4-phenylpiperazine |
| 12 | 4-(4-acetylphenyl)piperazine |
| 13 | 4-(3-trifluoromethylphenyl)piperazine |
| 14 | 4-(4-fluorophenyl)piperazine |
| 15 | 4-(4-nitrophenyl)piperazine |
| 16 | 4-(2-fluorophenyl)piperazine |

TABLE 21

[Structure: hydroxamic acid with phenyl-sulfonyl-phenyl-X-Ar]

| Example | X | Ar |
|---------|---|-----|
| 1 | O | 4-(1,2,4-triazol-1-yl)phenyl |
| 2 | O | 4-(1,2,4-triazol-1-yl)phenyl |
| 3 | O | 4-(pyrrol-1-yl)phenyl |
| 4 | O | 4-(piperidin-1-yl)phenyl |
| 5 | O | 4-(4-methylpiperazin-1-yl)phenyl |
| 6 | O | 4-(4-phenylpiperazin-1-yl)phenyl |
| 7 | O | 4-(4-phenylpiperidin-1-yl)phenyl |

TABLE 21-continued
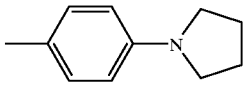
| Example | X | Ar |
|---|---|---|
| 8 | O | 4-(pyrrolidin-1-yl)phenyl |
| 9 | S | 4-(1,2,4-triazol-1-yl)phenyl |
| 10 | S | 4-(4H-1,2,4-triazol-4-yl)phenyl |
| 11 | S | 4-(pyrrol-1-yl)phenyl |
| 12 | S | 4-(piperidin-1-yl)phenyl |
TABLE 21-continued
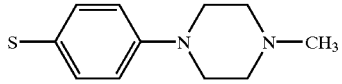
| Example | X | Ar |
|---|---|---|
| 13 | S | 4-(4-methylpiperazin-1-yl)phenyl |
| 14 | S | 4-(4-phenylpiperazin-1-yl)phenyl |
| 15 | S | 4-(4-phenylpiperidin-1-yl)phenyl |
| 16 | S | 4-(pyrrolidin-1-yl)phenyl |
TABLE 22
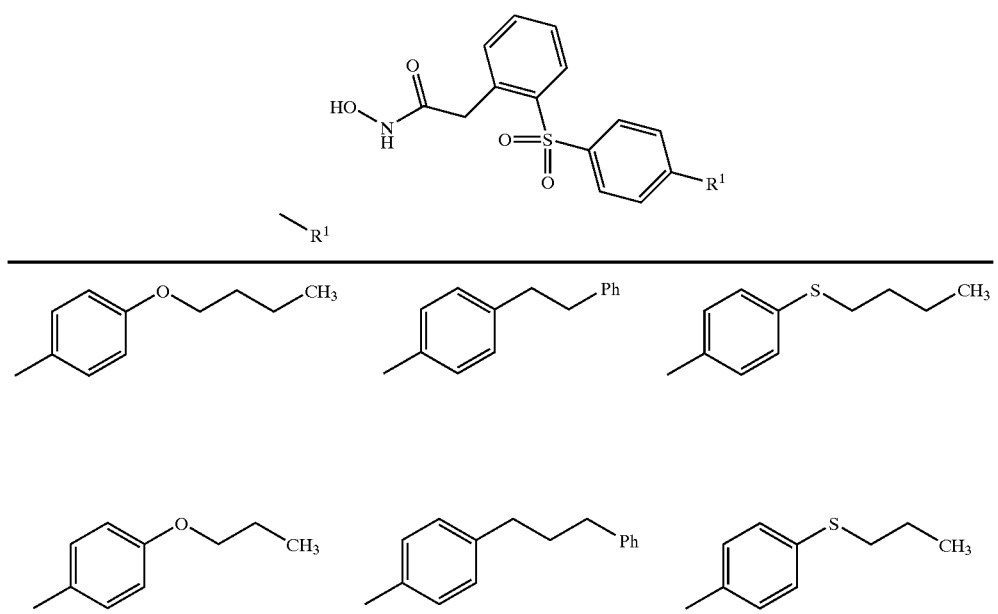

TABLE 22-continued
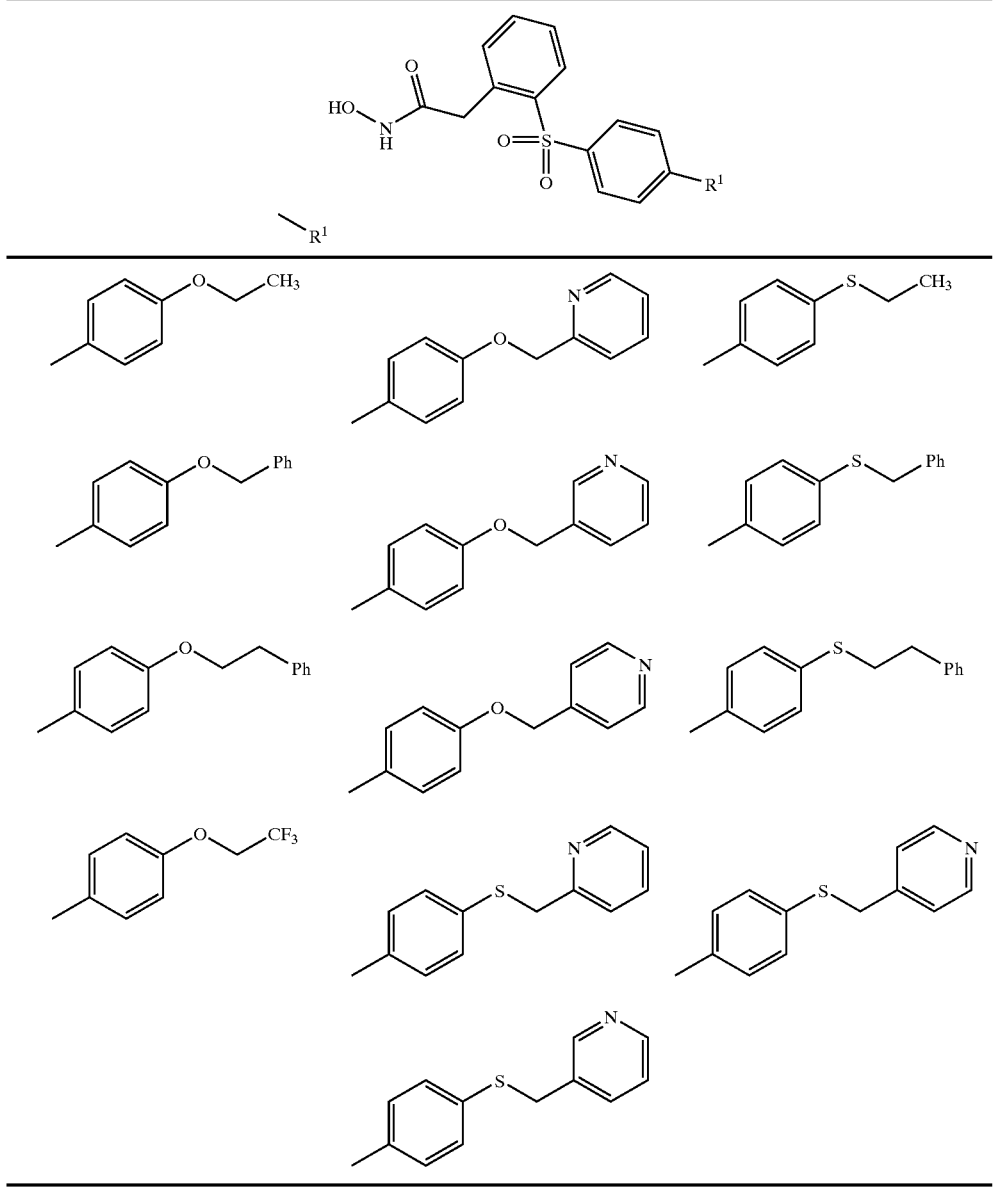
TABLE 23
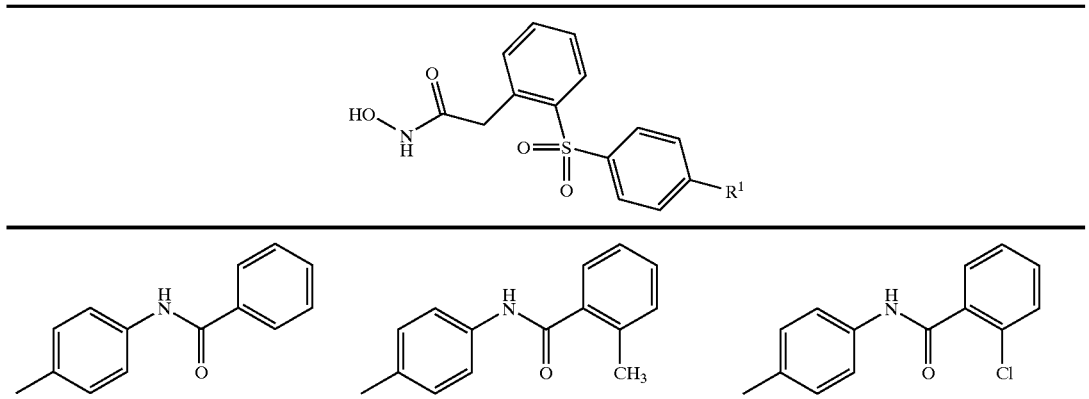

TABLE 23-continued
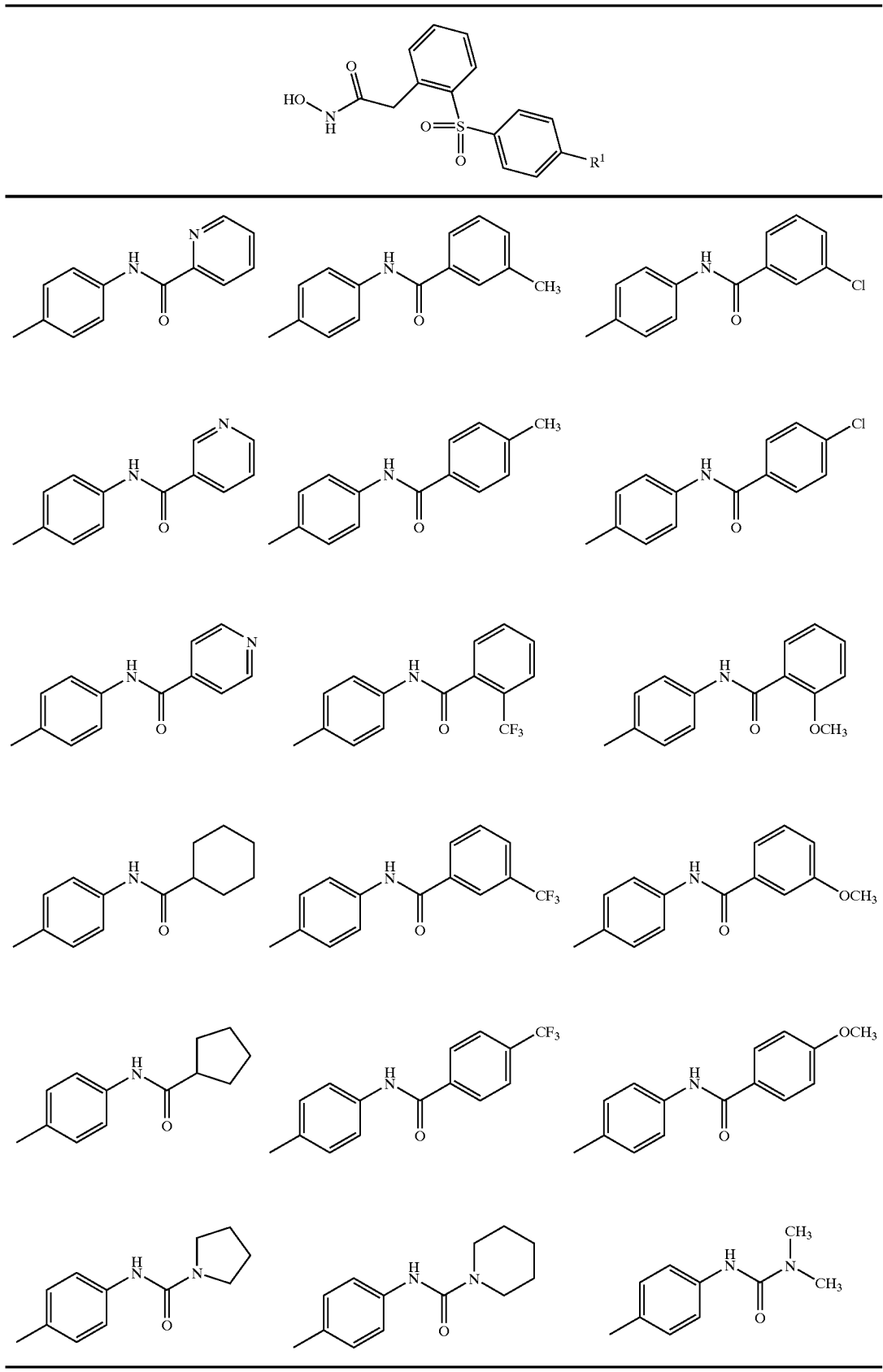

TABLE 24
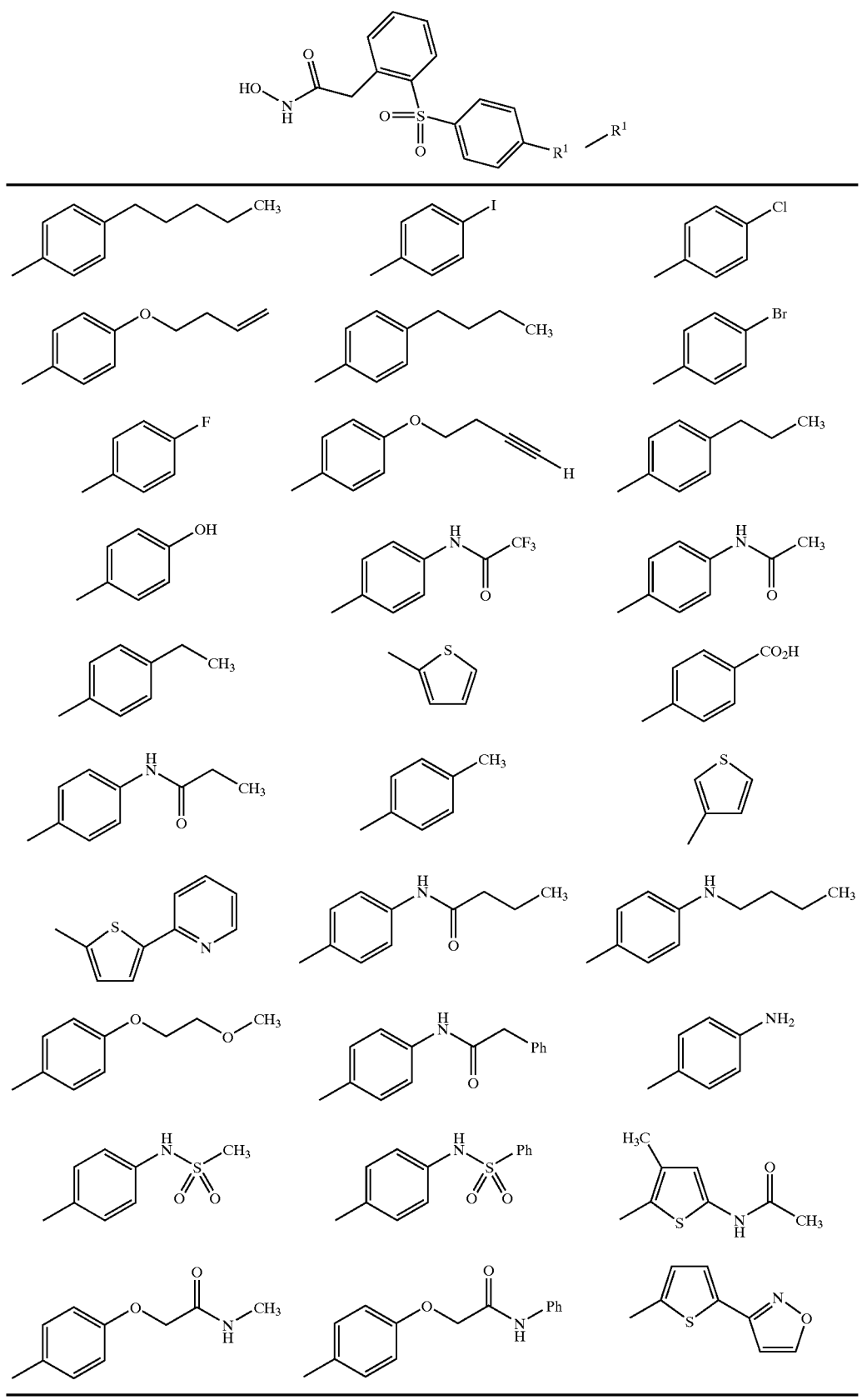

TABLE 25
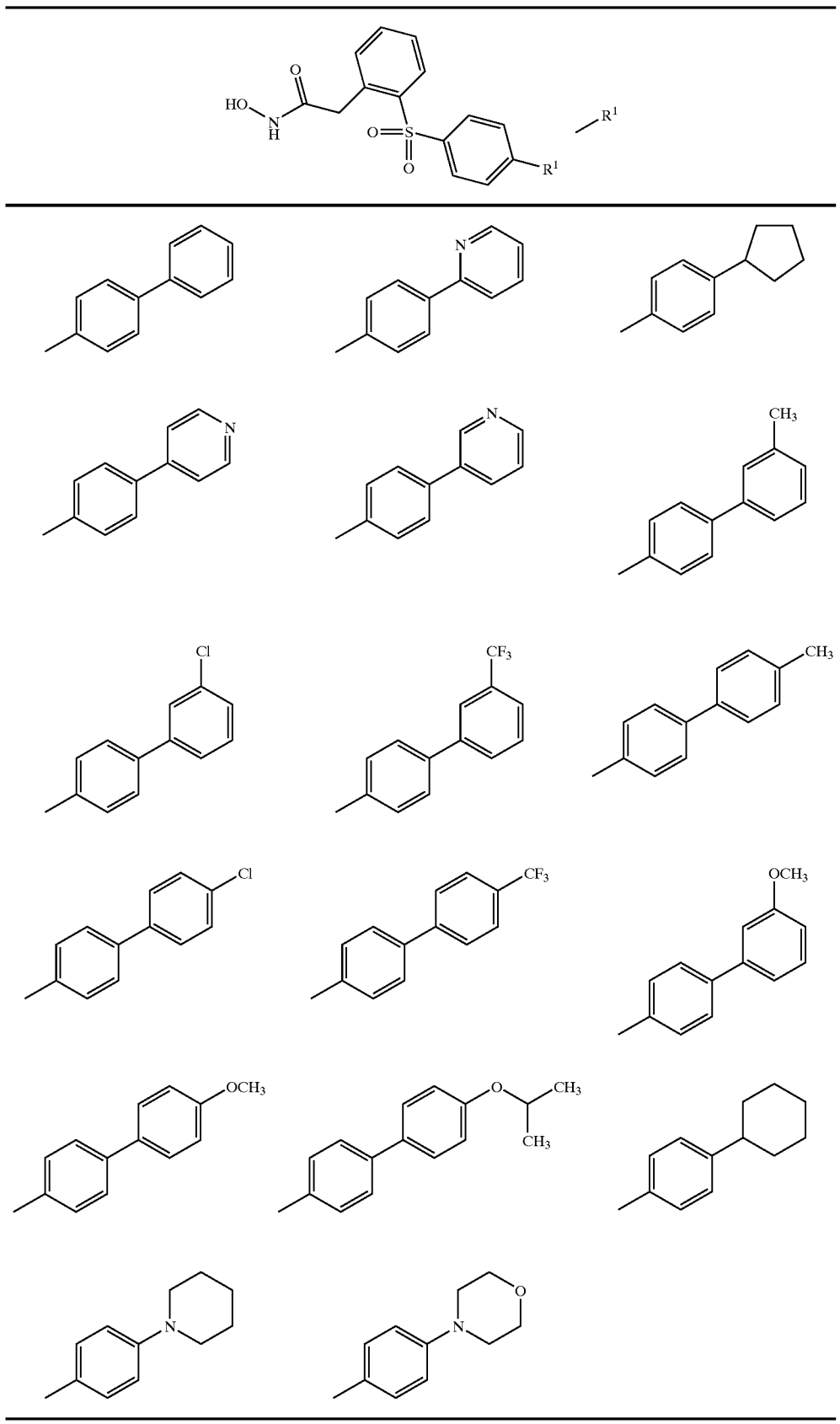

TABLE 26
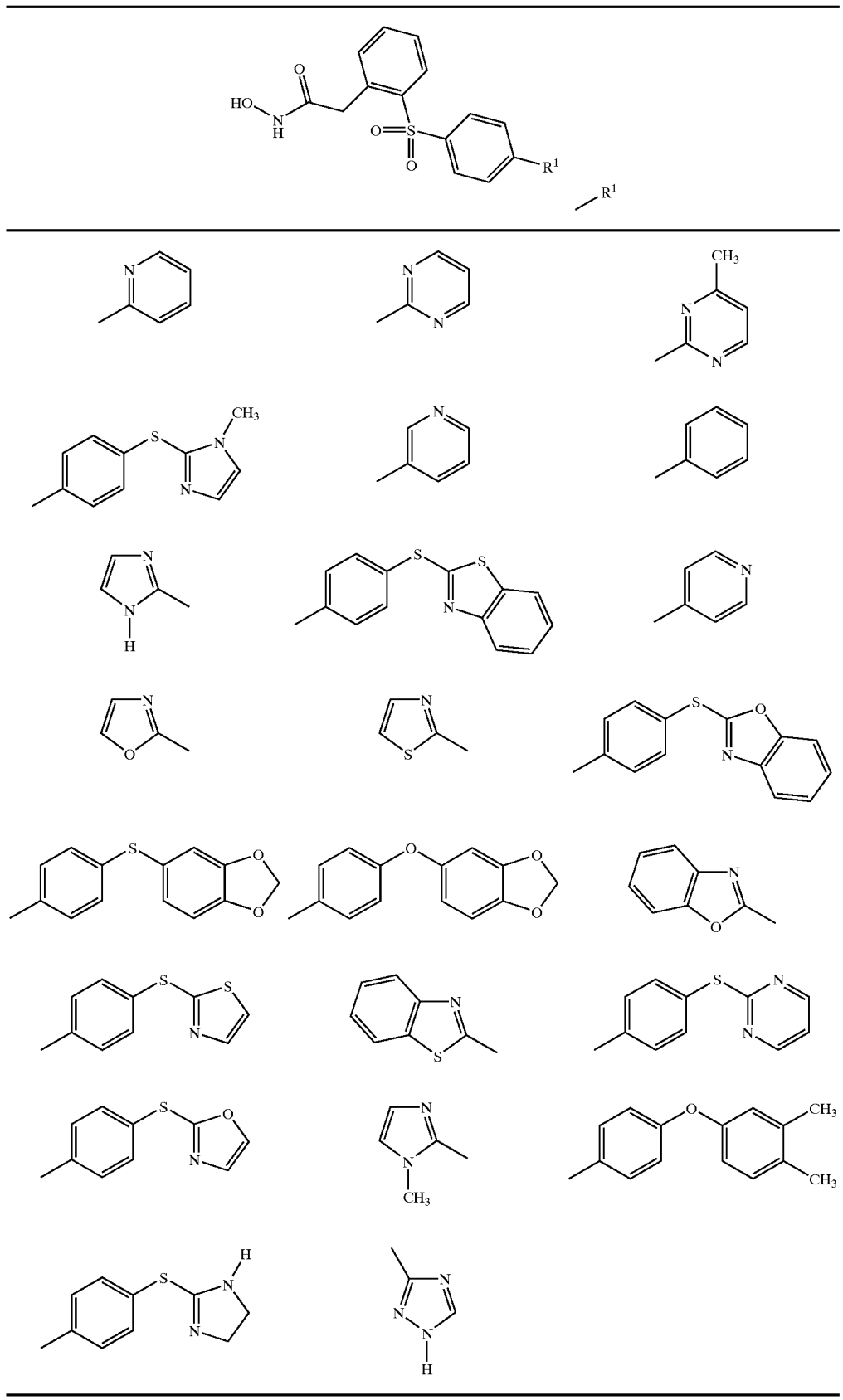

TABLE 27
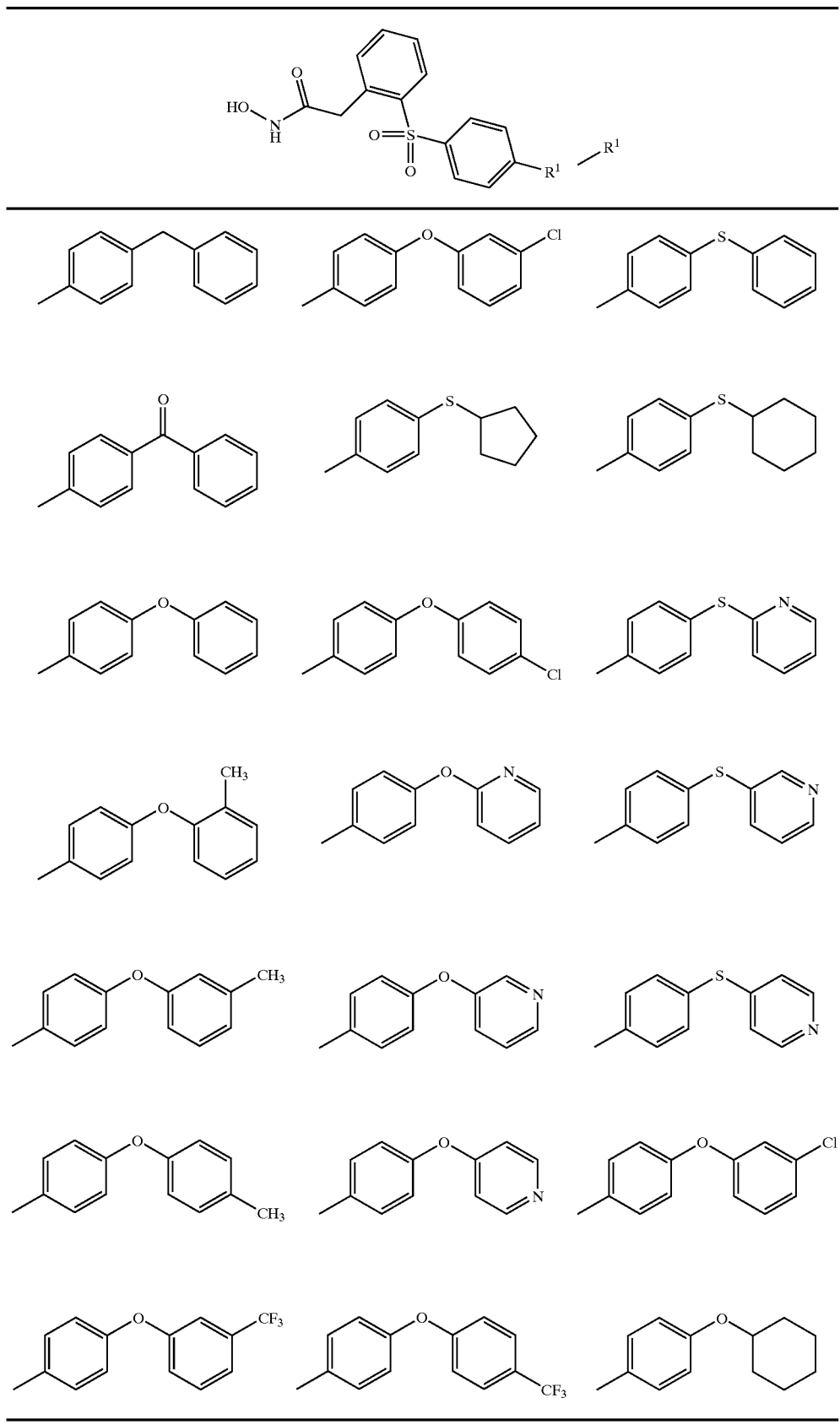

TABLE 28
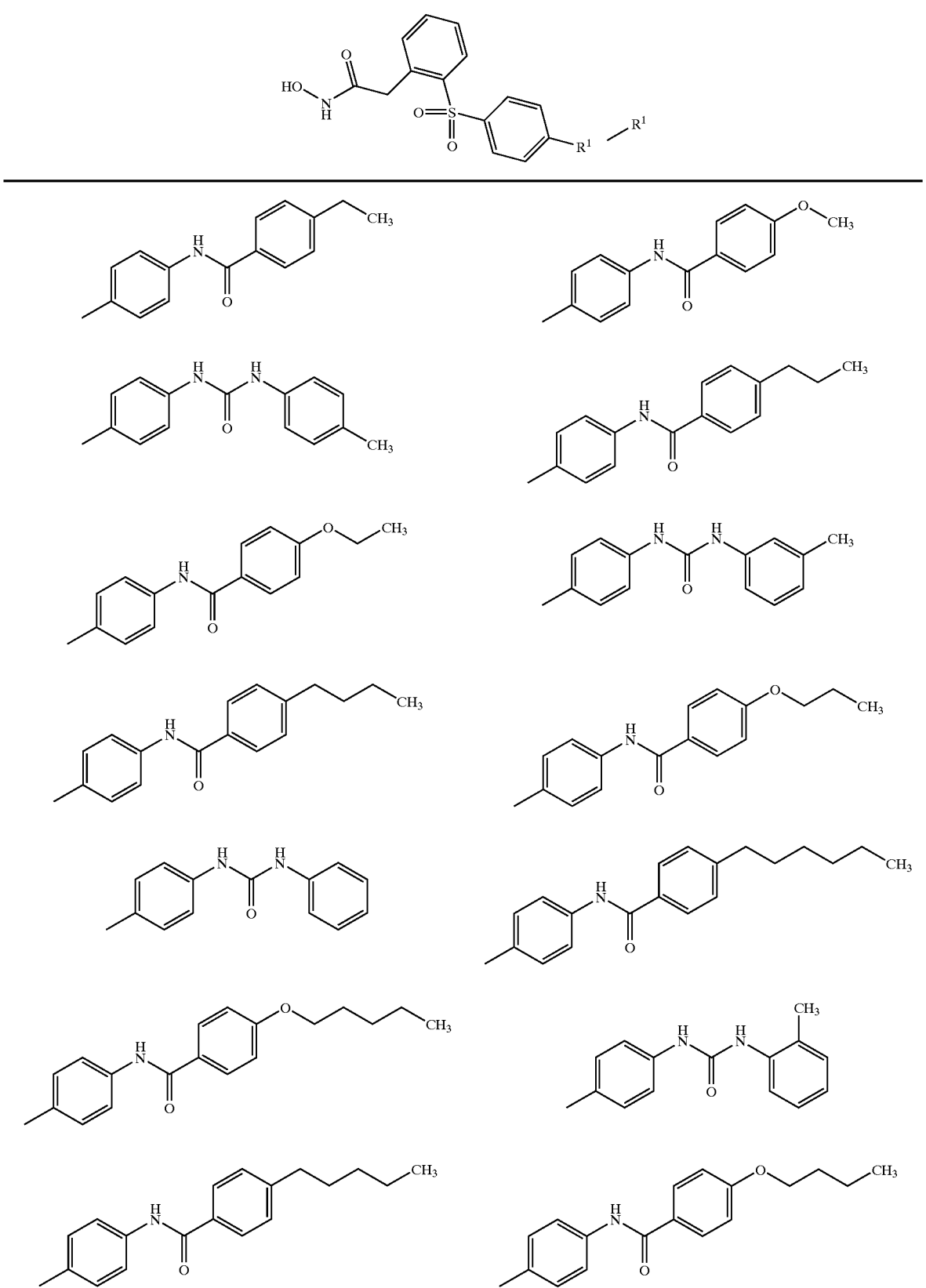

TABLE 28-continued
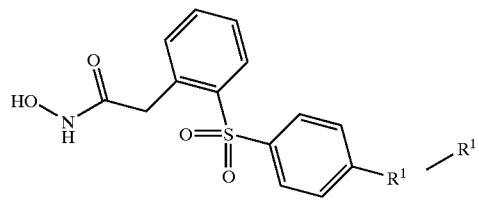
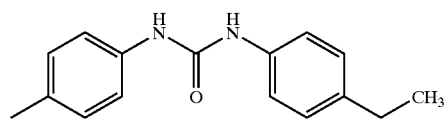
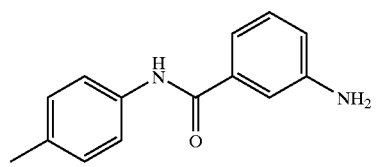
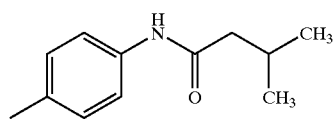
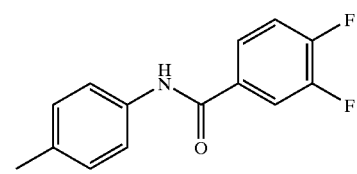
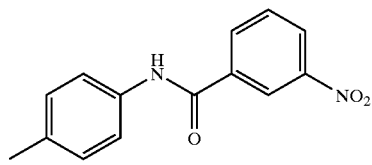
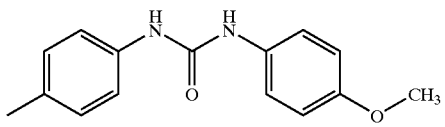
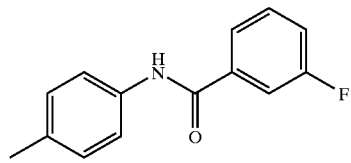
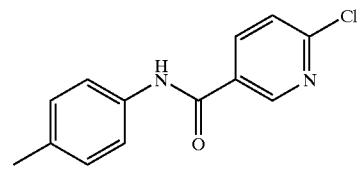
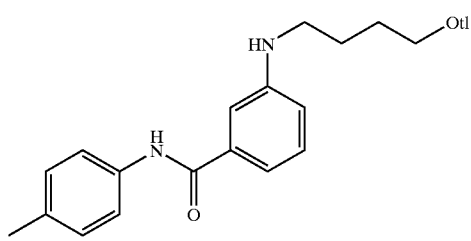
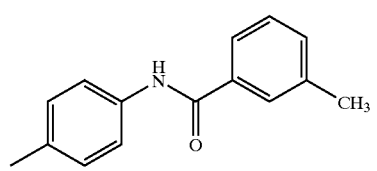
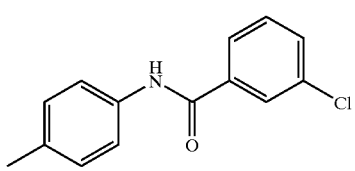

TABLE 29
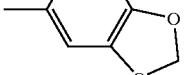
| Example | X | Ar |
|---|---|---|
| 1 | O | 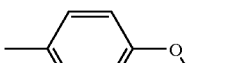 |
| 2 | O | 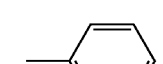 |
| 3 | S | 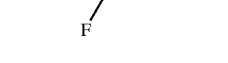 |
| 4 | S | 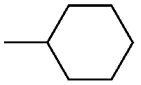 |
| 5 | S | 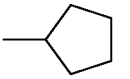 |
| 6 | S |  |
TABLE 30
| Example | R¹ R² | X | Ar |
|---|---|---|---|
| 1 |  | O |  |
| 2 |  | O | 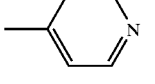 |
| 3 |  | O | 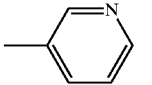 |
| 4 |  | O | 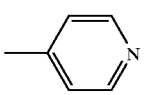 |
| 5 |  | O | 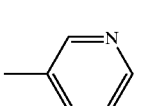 |
| 6 |  | O | 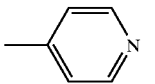 |
| 7 |  | O | 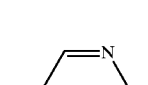 |
| 8 |  | O | 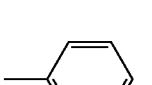 |
| 9 |  | S |  |
| 10 |  | S | 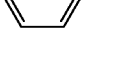 |
| 11 | | S | |

TABLE 31

[Structure: core compound with HO-NH-C(=O)- group, phenyl ring with SO2-C6H4-X-Ar substituent]

| Example | X | Ar |
|---------|---|-----|
| 1 | O | benzo[1,3]dioxole |
| 2 | O | 4-methoxyphenyl (–C6H4–O–CH3) |
| 3 | S | 4-fluorophenyl (–C6H4–F) |
| 4 | S | 4-methoxyphenyl (–C6H4–O–CH3) |
| 5 | S | phenyl |

Treatment Process

A process for treating a host mammal having a condition associated with pathological matrix metalloprotease activity is also contemplated. That process administering a compound described hereinbefore in an MMP enzyme-inhibiting effective amount to a mammalian host having such a condition. The use of administration repeated a plurality of time is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight daily, preferably about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tabled or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Preparation of Useful Compounds

Procedures are provided in the discussion and schemes that follow of exemplary chemical transformations that can be useful for the preparation of compounds of this invention. These syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under laboratory air.

Aryl and heteroaryl aryl compounds of this invention as define above by W can be prepared in a similar manner as is known to those skilled in the art. It should be understood that the discussion below refers to both aromatic systems, i.e., heteroaromatics and carbon aromatics, even though only one may be specifically mentioned.

In general, the choices of starting material and reaction conditions can vary as is well know to those skilled in the art. Usually, no single set of conditions is limiting because variations can be applied as required and selected by one skilled in the art. Conditions will also will be selected as desired to suit a specific purpose such as small scale preparations or large scale preparations. In either case, the use of less safe or less environmentally sound materials or reagents will usually be minimized. Examples of such less desirable materials are diazomethane, diethyl ether, heavy metal salts, dimethyl sulfide, some halogenated solvents, benzene and the like. In addition, many starting materials can be obtained from commericial sources from catalogs or through other arrangements.

An aromatic compound of this invention where y is 1 can be prepared as illustrated by converting a carbonyl group bonded to an aromatic (e.g.,benzene) ring ortho-substituted with a sulfide. The sulfide can be prepared via a nucleophilic displacement reaction of the ortho fluoride.

The nucleophile can be a thiol or thiolate anion prepared from a aryl thiol discussed below. A preferred thiol is 4-phenoxybenzenethiol converted in situ into its anion (thiolate) using potassium carbonate in iso-propyl alcohol at reflux temperature.

The carbonyl group can be a aldehyde, ketone or carboxylic acid derivative, i.e., a protected carboxylic acid or hydroxamate. A preferred carbonyl group is an aldehyde and a preferred aldehyde is 2-flourobenzaldehyde (ortho-fluorobenzaldehyde). A ketone can be converted by oxidation into an acid and/or an acid derivative using reagents such as those discussed below for oxidation of a sulfide or other methods well known in the art. It is noted that this oxidation can accomplish the oxidation of a sulfide intermediate into the corresponding sulfone in the same reaction system; i.e., in the same pot, if desired.

The carbonyl group can then be homologated if desired by reaction with an anion to form an addition compound. An example of a homologation reagent is a tri-substituted methane compound such as tetraethyl dimethylammonium-methylenediphosphonate or trimethylorthoformate. Tetraethyl dimethylammoniummethylenediphosphonate is preferred. Hydrolysis of the reaction product can provide a phenylacetic substituted on the aromatic ring with a sulfide of this invention. Acid hydrolysis is preferred. Acids and bases are discussed below and hydrochloric acid is preferred.

The sulfide can then be oxidized to form a sulfone in one or two steps as discused below. A preferred oxidizing agent is hydrogen peroxide in acetic acid. The carboxylic acid product or intermediate of this invention can then be converted into a protected derivative such as an ester or converted into an activated carboxyl group for reaction with hydroxylamine or and protected hydroxylamine; i.e., a hydroxamate. The conversion of an acid into a hydroxamate is discussed below as is the coupling process and removal of a protecting group if required.

The preferred protected hydroxamic acid derivative is the O-tetrahydropyranyl compound and the preferred coupling procedure utilizes a diimide (EDC), hydroxybenzotriazol and DMF solvent for the coupling reaction to form the intermediate hydroxybenzotriazol activated ester. A preferred reagent for removal of the THP protecting group is hydrochloric acid.

Alkylation of the acid at the carbon alpha to the carbonyl group to form the compounds of this invention can be carried out by first forming an anion using a base. Bases are discussed below. The preferred bases are strong bases that are either hindered and/or non-nucleophilic such as lithium amides, metal hydrides or lithium alkyls.

Following or during formation of the anion, an alkylating agent (an electrophile) is added that undergoes a nucleophilic substitution reaction. Non-limiting examples of such alkylating agents are haloalkanes, dihaloalkanes, haloalkanes also substituted by an activated ester group or activated esters and alkanes substitued with sulfate esters.

Activated ester groups are well known in the art and can include, for example, an activated ester of an alcohol or a halo compound, an ester of a haloalcohol such as a bromo-, iodo- or chloro-derivative of a tosylate, triflate or mesylate activated ester. Compounds wherein, for example, $R^2$ and $R^3$ are taken together as defined above, can be prepared using disubstituted alkylating agent; i.e., alkylating agents with two leaving groups in the same molecule. For example, 1,5-dihalo-diethylether or analogous reagents containing one or more sulfate ester leaving groups replacing one or more halogens can be used to form a pyran ring. A similar sulfur, nitrogen or protected nitrogen alkylating agent can be used to form a thiapyran or piperidine ring. A thiapyran can be oxidized to form a sulfoxide or a sulfone using methods discussed herein. A leaving group in an electrophilic reagent, as is well known in the art, can be a halogen such as chlorine, bromine or iodine or an active ester such as a sulfonate ester, e.g., toluenesulfonate (tosylate), triflate, mesylate and the like as discussed above.

The conversion of a cyclic amino acid, heterocycle or alpha-amino acid-defined by $R^2$ and $R^3$ that can include an amino acid (nitrogen heterocycle), which can be protected or unprotected, into a compound of this invention can be accomplished by alkylation or acylation. The carboxylic acid group can be protected with a group such as an alkyl ester such as methyl, ethyl, tert-butyl and the like or a tetrahydropyranyl ester or an arylalkyl ester such as benzyl or it can remain as a carboxylic acid. A protected amino acid such as an ethyl ester is preferred. The substituent on the heterocycle group is as defined above and can include hydrogen, tert-butoxycarbonyl (BOC or tBOC), benzyloxycarbonyl (Z) and iso-butyloxycarbonyl groups. In addition, the amine can be considered as being a protected intermediate as well as being a product of this invention when the N-substituent is not hydrogen.

The nitrogen substituent on the amino acid portion of the compounds of this invention can be varied. In addition, that variation can be accomplished at different stages in the synthetic sequence based on the needs and objectives of the skilled person preparing the compounds of this invention. The nitrogen side chain variations can include replacing the hydrogen substituent with a alkyl, arylalkyl, alkene or alkyne.

This can be accomplished by methods well known in the art such as alkylation of the amine with an electrophile such as halo- or sulfate ester (activated ester) derivative of the desired sidechain. An alkylation reaction is typically carried out in the presence of a base such as those discussed above and in a pure or mixed solvent as discussed above. A preferred base is postassium carbonate and a preferred solvent is DMF.

The alkenes, arylalkenes, arylalkynes and alkynes so formed can be reduced, for example, by hydrogenation with a metal catalyst and hydrogen, to an alkyl or arylalkyl compound of this invention and a alkyne or arylalkyne can be reduced to a alkene, arylalkene, arylakane or alkane with under catalytic hydrogenation conditions as discussed herein or with an deactivated metal catalyst. Catalysts can include, for example, Pd, Pd on Carbon, Pt, $PtO_2$ and the like. Less robust catalysts (deactivated) include such thing as Pd on $BaCO_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, lithium aluminum hydride. Alternatively, reductive alkylation can be carried out under hydrogenation conditions in the presence of a metal catalyst. Catalysts, hydrogen pressures and temperatures are discussed and are well known in the art. A preferred reductive alkylation catalyst is borane:pyridine complex.

In the case where an intermediate is a carboxylic acid, standard coupling reactions well known in the art can be used to form the compounds of this invention including protected intermediates. For example, the acid can be converted into an acid chloride, mixed anhydride or activated ester and reacted with an alcohol, amine, hydroxylamine or a protected hydroxylamine in the presence of base to form the amide, ester, hydroxamic acid,-protected hydroxamic acid. This is the same product as discussed above. Bases are discussed above and include N-methyl-morpholine, triethylamine and the like.

Coupling reactions of this nature are well known in the art and especially the art related to peptide and amino acid chemistry. Removal of the protecting group can be accomplished, if desired, using standard hydrolysis conditions such as base hydrolysis or exchange or acid exchange or hydrolysis as discussed.

The Schemes and/or dicussion also illustrate conversion of a carboxylic acid protected as an ester or amide into an hydroxamic acid derivative such as a O-arylalkylether or O-cycloalkoxyalkylether group such as the THP group. Methods of treating an acid or acid derivative with hydroxylamine or a hydroxylamine derivative to form a hydroxamic acid or hydroxamate derivative are discussed above. Hydroxylamine can be used in an exchange reaction by treatment of a precursor compound where the carboxyl is protected as an ester or amide with one or more equivalents of hydroxylamine hydrochloride or hydroxylamine at room temperature or above to provide a hydroxamic acid directly. The solvent or solvents, usually protic or protic solvent mixtures such as those listed herein.

This exchange process can be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranyl-hydroxyamine ($THPONH_2$), benzylhydroxylamine ($BnONH_2$), O-(trimethylsilyl) hydroxylamine and the like, in which case the compounds formed are tetrahydropyranyl (THP), benzyl (Bn) or TMS hydroxamic acid derivatives. Removal of the protecting groups when desired, for example, following further transformations in another part of the molecule or following storage, can be accomplished by standard methods well known in the art such as acid hydrolysis of the THP group as discussed above or reductive removal of the benzyl group with hydrogen and a metal catalyst such as palladium, platinum, palladium on carbon or nickel.

alpha-Amino acids or alpha-hydroxy carboxylic acids or protected carboxylic acids, hydroxamates or hydroxamic acid derivatives or intermediates (precursors) of this invention can be prepared by displacing, for example, a halogen, sulfate ester or other electrophile, from the alpha carbon of an acid or a derivative as listed. Methods for the halogenation of acids, esters, acid chlorides and like are well known in the art and include, for example, the HVZ reaction, treatment with $CuCl_2$, N-bromo- or N-chloro-succinimide, $I_2$, carbon tetraiodide or bromide and the like. The halogen can be displaced with a nucleophile in an $SN_2$ reaction. Nucleophiles can include hydroxide, ammonia or amines.

The aryl or heteroaryl carboxylic acids of this invention where Y is 0 and z is 1 can be prepared from heteroaryl or aryl fused lactones. An example of a fused lactone is phthalide. A preferred starting material is phthalide. This compound can be treated with an thiol, thiolate or metal—SH in order to undergo a $SN_2$ displacement at the methylene carbon to provide a sulfide or thiol compound of this invention or intermediate to a compound of this invention. A preferred thiol is 4-phenoxybenzenethiol that is used in the presence of potassium carbonate as a preferred base. The sulfide can be oxidized, before or after conversion of the acid to a hydroxamate or hydroxamic acid, to a sulfone of this invention. A preferred oxidizing agent is meta-chloroperbenzoic acid.

A preferred acid activating group is the chloride prepared by reaction of an acid with oxalyl chloride as a preferred reagent. A phthalide or a heteroaryl analog of a phthalide can be treated with a Lewis acid such as zinc chloride or zinc bromide along with a halogenating reagent such as phosphorus trichloride or thionyl bromide or the like to form a ortho-(haloalkyl)-aryl acid or ortho-(haloalkyl)-heteroaryl acid derivative. Examples include bromomethyl acid bromides and chloromethyl acid chlorides. These carboxylic acids can be derivatized with protecting groups, hydroxamic acids or hydroxamic acid precursors (hydroxamates) or hydrolyzed to the acid as required. A preferred hydroxamate forming reagent is O-(trimethylsilyl)hydroxylamine (TMS-hydroxylamine) and removal of the TMS protecting group is preferably accomplished by acid hydrolysis using hydrochloric acid.

Displacement ($SN_2$) of the halogen in this example by a thiol in the presence of base or a preformed thiolate can be accomplished as discussed and/or shown and as is well known in the art. Again, oxidation of the sulfide can be carried out before or after derivatization of the carboxylic acid as discussed to prepare the hydroxamic acids of this invention. Removal of the protecting groups can be carried out using acid hydrolysis or reduction as discussed elsewhere in this document.

The alcohols of this invention can be protected or deprotected as required or desired. Protecting groups can include THP ethers, acylated compounds and various silyl derivatives. These groups, including there protection and removal, are well known in the art.

Examples of bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like.

Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N', N',-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl, phenyl, butyl, iso-butyl, sec-butyl or tert-butyl lithium, nodium or potassium salts of dimethylsulfoxide, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents. Preferred base for use in the alkylation reaction is lithium diisopropyl amide as mentioned above.

Reaction media in general can be comprised of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like.

Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like. Room temperature or less or moderate warming (−10° C. to 60° C.) are the preferred temperatures of the reaction. If desired, the reaction temperature might be about −78° C. to the reflux point of the reaction solvent or solvents. The preferred solvent for an alkylation reaction is tetrahydrofurane (THF).

Acids are used in many reactions during various synthesis. The Schemes as well as this discussion preparative methods illustrate acid use for the removal of the THP protecting group to produce a hydroxamic acid, removal of a tert-butoxy carbonyl group, hydroxylamine/ester exchange and the like. Acid hydrolysis of carboxylic acid protecting groups or derivatives is well known in the art. These methods, as is well known in the art, can use acid or acidic catalysts. The acid can be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like.

Contemplated compounds can include compounds wherein a nitrogen of an amine is acylated to provide, for example, amino acid carbamates. Non-limiting examples of these carbamates are the carbobenzoxycarbonyl (Z, CBZ, benzyloxycarbonyl), iso-butoxycarbonyl and tert-butoxycarbonyl (BOC, t-BOC) compounds. The materials can be made, as discussed above, at various stages in the synthesis based on the needs and decisions made by a person skilled in the art using methods well know in the art.

Useful synthetic techniques and reagents include those used in protein, peptide and amino acid synthesis, coupling and transformation chemistry. The use of the tert-butoxycarbonyl (BOC) and benzyloxycarbonyl (Z) as will as their synthesis and removal are examples of such protection or synthesis schemes. Transformations of amino acids, amino esters, amino acid hydroxamates, amino acid hydroxamate derivatives and amino acid amides of this invention or compounds used in this invention is discussed herein or/and shown in the schemes. This includes, for example, active ester or mixed anhydride couplings wherein preferred bases, if required, are tertiary amines such as N-methylmorpholine. Reagents for protection of the amine group of the protected amino acids include carbobenzoxy chloride, iso-butylchloroformate, tert-butoxycarbonyl chloride, di-tert-butyl dicarbonate and the like which are reacted with the amine in non-protic or dipolar aprotic solvents such as DMF or THF or mixtures of solvents.

Removal of protecting groups such as carbamates, silyl groups and benzyl, p-methoxybenzyl, or other substituted benzyl groups or diphenylmethyl (benzhydryl) or triphenylmethyl (trityl) can be carried out at different stages in the synthesis of the compounds of this invention as required by methods selected by one skilled in the art. These methods are well known in the art including the amino acid, amino acid coupling, peptide synthesis, peptide mimetic synthesis art.

Removal methods can include catalytic hydrogenation, base hydrolysis, carbonyl addition reactions, acid hydrolysis and the like. Both the preparation and removal of protecting groups, for example, carbamates, benzyl groups and/or substitued arylalkyl groups is discussed in Green, T., *Protecting Groups in Organic Chemistry*, Second ed., John Wiley & Sons, New York (1991). A preferred method of removal of a BOC group is HCl gas in methylene chloride which, following normal workup, provides directly an HCl salt of an aminoacid of this invention.

Sulfone compounds such as those where $R^1$ is nitrobenzene can be prepared as compounds of this invention by synthesis of a thiol, displacement of an electrophile by the nucleophilic thiol or thiolate and oxidation of the product thiol ether to the sulfone. For example, displacement of the electrophilic group with a nitro-benzene thiol can yield a compound where $R^1$ is nitrobenzene, whose nitro group can be reduced to provide a useful amino compound wherein $R^1$ is an aniline. It should be noted that nitrobenzenethiol is an example and not to be considered as limiting or required. Oxidation of the thioether product can be carried out as discussed below when desired.

The reduction of nitro groups to amines is well known in the art with a preferred method being hydrogenation. There is usually a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred.

The resulting amino group can be alkylated if desired. It can also be acylated with, for example, an aroyl chloride, heteroaryl chloride or other amine carbonyl forming agent to form an $R^1$ amide of this invention. The amino sulfone or thioether can also be reacted with a carbonic acid ester chloride, a sulfonyl chloride, a carbamoyl chloride or an isocyanate to produce the corresponding carbamate, sulfonamides, or ureas of this invention. Acylation of amines of this type are well known in the art and the reagents are also well known.

Usually these reactions are carried out in aprotic solvents under an inert or/and dry atmosphere at about 45° C. to about −10° C. An equivalent of a non-competitive base is usually used with sulfonyl chloride, acid chloride or carbonyl chloride reagents. Following or before this acylation step, synthesis of the hydroxamic acid products of this invention can proceed as discussed.

Other thiol reagents can also be used in the preparation of compounds of this invention. Examples are fluoroaryl, fluoroheteroaryl, azidoaryl or azidoheteroaryl or heteroaryl thiol reagents. These thiols can be used a nucleophiles to as discussed above. Oxidation to the corresponding sulfone can then be carried out.

The sulfones, if substituted by a hydrazine or substituted hydrazine, can be oxidized to a hydrazone of this invention. The fluoro substituted sulfone can be treated with a nucleophile such as ammonia, a primary amine, a quaternary ammonium or metal azide salt or a hydrazine under pressure if desired, to provide an azido, amino, substituted amino or hydrazino group. Azides can be reduced to an amino group using, for example, hydrogen with a metal catalyst or metal chelate catalyst or by an activated hydride transfer reagent. The amines can be acylated as discussed above.

Methods of preparing useful aminethiol intermediates include protection of an aromatic or heteroaromatic thiol with trityl chloride to form the trityl thiol derivative, treatment of the amine with as reagent such as an aromatic or heteraromatic acid chloride to form the amide, removal of the trityl group, with acid to form the thiol. Acylating agents include benzoyl chloride and trityl removing reagents include triflouroacetic acid and trisiopropylsilane.

The fluorine on the fluorosulfones of this invention can also be displaced with other aryl or heteroaryl nucleophiles for form compounds of this invention. Examples of such nucleophiles include salts of phenols, thiophenols, —OH group containing aromatic heterocyclic compounds or —SH containing heteroaryl compounds. Tautomers of such groups azo, hydrazo, —OH or —SH are specifically included as useful isomers.

A preferred method of preparing intermediates in the synthesis of the substituted sulfones is by oxidation of an appropriate acetophenone, prepared from a flouroacetophenone, with for example, peroxymonosulfate, to form the corresponding phenol-ether. The phenol-ether is converted into its dimethylthiocarbamoyl derivative using dimethylthiocarbamoyl chloride, rearranged into the dimethylthiocarbamoyl derivative with heat to provide the thiol required for preparation of the thioether intermediate discussed and/or shown in the schemes.

The compounds of this invention including protected compounds or intermediates can be oxidized to the sulfones as shown in the schemes and/or discussed above. The selection of the stage of the alternative synthesis to implement this conversion of sulfides into the sulfones or sulfoxides can be carried out by one skilled in the art.

Reagents for this oxidation process may, in a non-limiting example, include peroxymonosulfate (OXONE®), hydrogen peroxide, meta-chloroperbenzoic acid, perbenzoic acid, peracetic acid, perlactic acid, tert-butyl peroxide, tert-butyl hydroperoxide, tert-butyl hypochlorite, sodium hypochlorite, hypochlorus acid, sodium meta-peroiodate, periodic acid, ozone and the like. Protic, non-protic, dipolar aprotic solvents, either pure or mixed, can be chosen, for example, methanol/water. The oxidation can be carried out at temperature of about −78° to about 50° degrees centigrade and normally selected from a range −10° C. to about 40° C.

Preparation of the sulfones can also be carried out in two steps by the oxidation of a sulfide to a sulfoxide followed by oxidation of the sulfoxide to the sulfone. This can occur in one pot or by isolation of the sulfoxide. This latter oxidation can be carried out in a manner similar to the oxidation directly to the sulfone except that about one equivalent of oxidizing agent can be used preferably at a lower temperature such as about 0° C. Preferred oxidizing agents include peroxymonosulfate and meta-chloroperbenzoic acid.

Salts of the compounds or intermediates of this invention are prepared in the normal manner wherein acidic compounds are reacted with bases such as those discussed above to produce metal or nitrogen containing cation salts. Basic compounds such as amines can be treated with an acid to form an amine salt.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base.

Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient since the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention. Examples include cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for drug delivery.

Where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

The chemical reactions described above are generally disclosed in terms of their broadest application to the preparation of the compounds of this invention. Occasionally, the reactions can not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Other compounds of this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

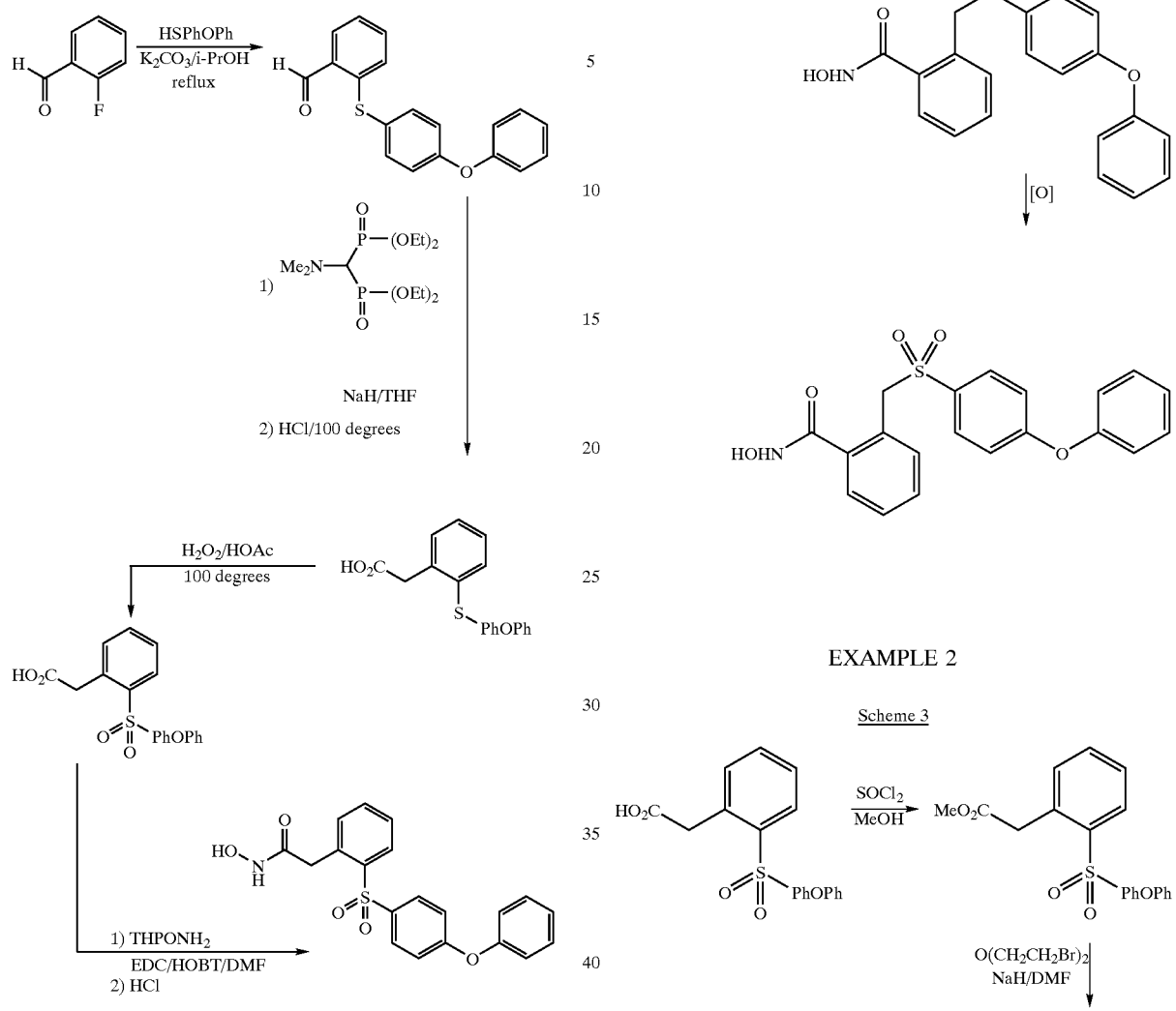
EXAMPLE 2
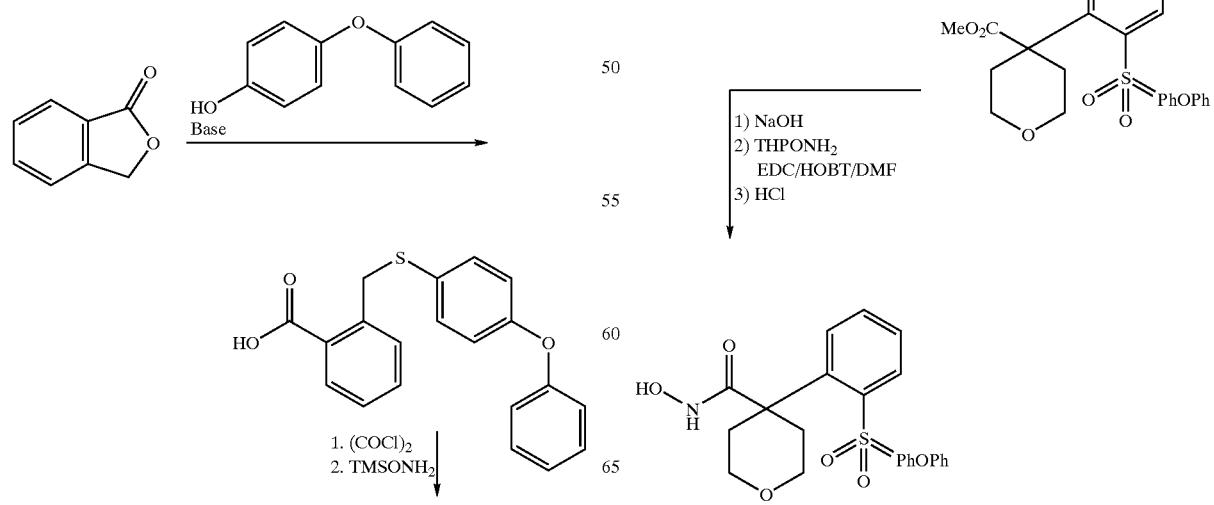

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

N-hydroxy-2-[[(4-phenoxyphenyl)-sulfonyl]methyl] benzamide

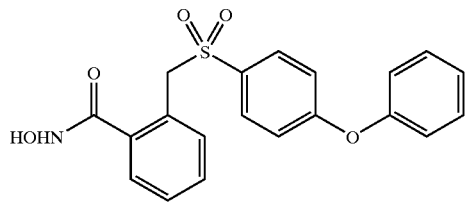

Part A: To a solution of phthalide (6.30 g, 47.0 mmol) in DMF (100 mL) was added $K_2CO_3$ (10.0 g, 49.4 mmol) and 4-(phenoxy)benzenethiol (9.59 g, 49.4 mmol) and the solution was heated to one hundred degrees Celsius for 2 hours. The solution was diluted with $H_2O$ and acidified with 1N HCl to pH=1. The resulting tan solid was collected and washed with $H_2O$. The solid was dissolved into ethyl ether and dried over $MgSO_4$. Concentration in vacuo followed by recrystallization (ethyl ether/hexane) provided the sulfide as a white solid (9.12 g, 58%). MS(CI) $MH^+$ calculated for $C_{20}H_{16}O_3S$: 337, found 337. Analytical calculation for $C_{20}H_{16}O_3S$: C, 71.41; H, 4.79; S, 9.53. Found: C, 71.28; H, 4.67; S, 9.19.

Part B: To a solution of the sulfide of part A (3.00 g, 8.92 mmol) in dichloromethane (28 mL) and DMF (1 drop) was added oxalyl chloride (1.08 mL, 12.4 mmol) and the solution was stirred for 1 hour. After concentration in vacuo the residue was dissolved into dichloromethane (16 mL) and the solution was cooled to zero degrees Celsius. Tetramethylsilyl hydroxylamine (2.55 mL, 20.8 mmol) was added and the solution was stirred for 1.5 hours. The solution was diluted with dichloromethane and washed with 1N HCl, $H_2O$ and saturated NaCl and dried over $MgSO_4$. Chromatography (on silica, ethyl acetate/hexane/toluene) provide the hydroxylamine as a clear paste (970 mg, 31%).

Part C: To a solution of the hydroxylamine of part B (970 mg, 2.76 mmol) in dichloromethane (25 mL) cooled to zero degrees Celsius was added 3-chloroperbenzoic acid (60%, 2.14 g, 7.45 mmol) and the solution was stirred for 3 hours at ambient temperature. The solution was diluted with ethyl ether and washed with saturated $Na_2SO_3$, saturated $NaHCO_3$ and saturated NaCl and dried over $MgSO_4$. Reverse phase chromatography (on silica, acetonitrile/$H_2O$) provided the title compound as a white solid (345 mg, 33%). MS(CI) $MH^+$ calculated for $C_{20}H_{17}NO_5S$: 384, found 384. Analytical calculation for $C_{20}H_{17}NO_5S \cdot 0.3H_2O$: C, 61.70; H, 4.56; N, 3.60; S, 8.25. Found: C, 61.74; H, 4.42; N, 3.61; S, 8.31.

EXAMPLE 2

N-hydroxy-2-[(4-phenoxyphenyl)-sulfonyl] benzeneacetamide

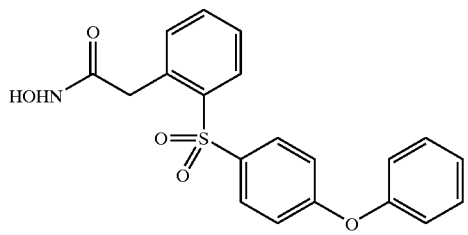

Part A: To a solution of 4-(phenoxy)benzenethiol (6.06 g, 30.0 mmol) and $K_2CO_3$ (4.55 g, 33.0 mmol) in isopropanol (30 mL) was added 2-fluorobenzaldehyde (3.2 mL, 30.0 mmol). The solution was refluxed for 20 hours. The reaction was quenched by the addition of ice-$H_2O$ and was extracted with $CHCl_3$. The organic layer was dried over $MgSO_4$. Filtration through a pad of silica gel provided the sulfide as a yellow solid (7.43 g, 81%).

Part B: A solution of NaH (60% dispersion in mineral oil, washed with hexane, 264 mg, 6.6 mmol) in THF (12 mL) was cooled to zero degrees Celsius and tetraethyl dimethylammoniummethylene diphosphonate (1.99 g, 6.0 mmol) was added. The solution was warmed to ambient temperature and the sulfide of part A (1.84 g, 6.0 mmol) was added. The solution was stirred for 4 hours at ambient temperature. The solution was extracted with ethyl acetate and washed with $H_2O$ and dried over $MgSO_4$. Concentration in vacuo provided a brown oil which was dissolved in 6M HCl (10 mL) and the solution was heated to one hundred degrees Celsius for 1 hour. The solution was extracted with $CHCl_3$ and the organic layer was dried over $MgSO_4$. Concentration in vacuo provided the acid as an oil (918 mg, 48%).

Part C: To a solution of the acid of part B (918 mg, 3 mmol) in acetic acid (30 mL) was added 30% hydrogen peroxide (1.2 mL, 12 mmol) and the solution was heated to one hundred degrees Celsius for 40 minutes. The solution was lyophilized and chromatography (hexane/ethyl acetate) provided the sulfone as a foam (697 mg, 63%).

Part D: To a solution of the sulfone of part C (695 mg, 1.89 mmol) in acetonitrile (2 mL) was added tetrahydropyranyl hydroxylamine (270 mg, 2.3 mmol). After 5 minutes EDC (442 mg, 2.3 mmol) was added and the solution was stirred for 3 hours. The solution was concentrated in vacuo and the residue was partitioned between ethyl acetate and $H_2O$. The organic layer was dried over $MgSO_4$. Chromatography (on silica gel, ethyl acetate/hexane) provided the ester as a white foam (688 mg, 77%).

Part E: To a solution of the ester of part D (565 mg, 1.2 mmol) in methanol (10 mL) was added p-toluenesulfonic acid (25 mg) and the solution was stirred at ambient temperature for 2 hours. The solution was concentrated in vacuo and chromatography (chloroform/methanol) provided the title compound as a white solid (339 mg, 74%).

Comparative Examples

EXAMPLE 3

N-hydroxy-2-[[4-(phenylmethyl)-1-piperidinyl]sulfonyl]benzamide

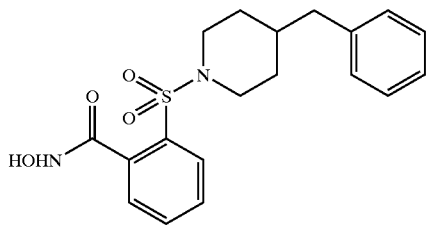

Part A: To a solution of 2-chlorosulfonyl-benzoic acid ethyl ester, prepared per Nagasawa, et. al. J. Med. Chem. 1995, 38, 1865–1871, (5.80 g, 23.0 mmol) in acetonitrile (50 mL) was added 4-benzylpiperidine (4.38 mL, 25 mmol), triethylamine (3.78 mL, 27 mmol) and 4-dimethylaminopyridine (50 mg). The solution was stirred for 4 hours at ambient temperature and concentrated in vacuo. The residue was dissolved into 1N HCl and extracted with ethyl acetate. The organic layer was dried over $MgSO_4$ and filtered through a pad of silica gel to provide the sulfonamide as an oil (7.45 g, 84%).

Part B: To a solution of the sulfonamide of part A (1.08 g, 2.80 mmol) in methanol (50 mL) and $H_2O$ (20 mL) was added KOH (2 g) and the solution was stirred for 3 hours at ambient temperature. The solution was concentrated in vacuo and the remaining aqueous solution was acidified with 1N HCl. The solution was extracted with chloroform and the organic layer was dried over $MgSO_4$ and filtered through a pad of silica gel. Concentration in vacuo provided the acid as a white foam (996 mg, quantitative yield).

Part C: To a solution of the acid of part B (415 mg, 1.2 mmol) in acetonitrile (2 mL) was added tetrahydropyranyl hydroxylamine (200 mg, 1.7 mmol). After the solution was stirred for 5 minutes EDC (325 mg, 1.7 mmol) was added and the solution was stirred for 3 hours at ambient temperature. The solution was concentrated in vacuo and the residue was dissolved into $H_2O$ and extracted with ethyl acetate. The organic layer was dried over $MgSO_4$. Chromatography (on silica, ethyl acetate/hexane) provided the ester as a white solid (437 mg, 82%).

Part D: To a solution of the ester of part C (437 mg, 0.98 mmol) in methanol (5 mL) was added p-toluenesulfonic acid (40 mg) and the solution was stirred for 1 hour at ambient temperature. The solution was concentrated in vacuo. Chromatography (ethyl acetate,1% $NH_4OH$) provided the title compound as an oil (122 mg, 34%).

EXAMPLE 4

2-[([1,1'-biphenyl]-4-ylmethyl)-sulfonyl]-N-hydroxybenzamide

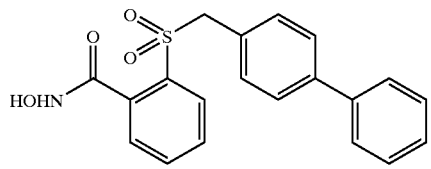

Part A: To a solution of thiosalicylic acid (5.00 g, 32.4 mmol) and 4-phenylbenzyl chloride (6.57 g, 32.4 mmol) in ethanol (81 mL) and $H_2O$ (40 mL) was added $K_2CO_3$ (4.48 g, 32.4 mmol) and the solution was heated to reflux for 2 hours. Upon cooling to ambient temperature a white solid formed. To this mixture is added 1N HCl (200 mL) and vacuum filtration provided the sulfide as a white solid (7.32 g, 70%).

Part B: To a solution of the sulfide of part A (1.00 g, 3.12 mmol) in formic acid (17 mL) heated to fifty degrees Celsius was added 30% hydrogen peroxide (1.16 mL). The solution was stirred at fifty-five degrees Celsius for 3 hours followed by 40 hours at ambient temperature. The solution was concentrated and reverse phase chromatography (acetonitrile/$H_2O$) provided the sulfone as a white solid (500 mg, 45%).

Part C: To a solution of the sulfone of part B (500 mg, 1.42 mmol) in DMF (2.8 mL) was added tetrahydropyranyl hydroxylamine (173 mg, 1.48 mmol), N-hydroxybenzotriazole (211 mg, 1.56 mmol) and EDC (299 mg, 1.56 mmol) and the solution was stirred for 18 hours at ambient temperature. The solution was concentrated in vacuo and the residue was dissolved into $H_2O$. The solution was extracted with ethyl acetate and the organic layer was washed with 1N HCl, saturated $NaHCO_3$, $H_2O$ and saturated NaCl and dried over $MgSO_4$. Concentrated in vacuo provided the ester as a white solid (571 mg, 89%). MS(CI) MH$^+$ calculated for $C_{25}H_{25}NO_5S$: 452, found 452.

Part D: To a solution of the ester of part C (570 mg, 1.26 mmol) in methanol (10 mL) was added p-toluenesulfonic acid (15 mg) and the solution was stirred at ambient temperature for 1.5 hours. The solution was concentrated in vacuo and reverse phase chromatography (acetonitrile/$H_2O$) provided the title compound as a white solid (244 mg, 53%). MS(EI) M$^+$ calculated for $C_{20}H_{17}NO_4S$: 367, found 367. Analytical calculation for $C_{20}H_{17}NO_4S$: C, 65.38; H, 4.66; N, 3.81. Found: C, 65.01; H, 4.64; N, 4.04.

EXAMPLE 5

N-hydroxy-2-[[(4-phenoxyphenyl)-sulfonyl]amino]benzamide

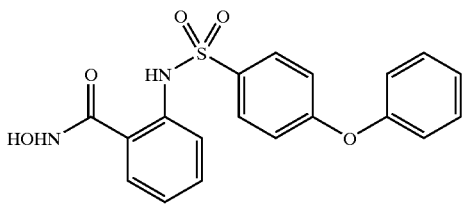

Part A: To a solution of isatoic anhydride (1.00 g, 6.13 mmol) in acetonitrile (3 mL) was added tetrahydropyranyl hydroxylamine (1.56 g, 6.74 mmol) and the solution was heated to reflux for 2 hours. The solution was concentrated in vacuo and recrystallization of the residue (ethyl acetate/hexane) provided the ester as a white solid (760 mg, 52%). MS(CI) MH+ calculated for $C_{12}H_{16}N_2O_3$: 237, found 237. Analytical calculation for $C_{12}H_{16}N_2O_3$: C, 61.00; H, 6.83; N, 11.86. Found: C, 60.82; H, 6.95; N, 11.76.

Part B: To a solution of 4-(phenoxy)benzene sulfonyl chloride, prepared per J. Am. Chem. Soc., 1931, 93, 1112–1115) (341 mg, 1.27 mmol) in pyridine (2 mL) cooled to zero degrees Celsius was added the ester of part B (300 mg, 1.27 mmol) and the solution was stirred at zero degrees Celsius for 3 hours. The solution was concentrated in vacuo and the residue was dissolved in 1N HCl and was extracted with ethyl acetate. The organic layer was washed with 1N HCl, $H_2O$ and saturated NaCl and dried over $MgSO_4$. Chromatography (on silica gel, ethyl acetate/hexane) provided the sulfone as a white solid (321 mg, 54%). MS(CI) MH+ calculated for $C_{24}H_{24}N_2O_6S$: 469, found 469. Analytical calculation for $C_{24}H_{24}N_2O_6S$: C, 61.53; H, 5.16; N, 5.98; S, 6.84. Found: C, 61.10; H, 4.93; N, 5.86; S, 6.41.

Part C: Into a solution of the sulfone of part B (320 mg, 0.68 mmol) in methanol (3 mL) cooled to zero degrees Celsius was bubbled HCl gas for 5 minutes. The solution was concentrated in vacuo and the residue was triturated with ethyl ether. Collection by vacuum filtration provided the title compound as a pink solid (163 mg, 62%). MS(CI) MH+ calculated for $C_{19}H_{16}N_2O_4S$: 385, found 385. Analytical calculation for $C_{19}H_{16}N_2O_6S.0.2H_2O$: C, 58.81; H, 4.26; N, 7.22; S, 8.26. Found: C, 58.88; H, 4.37; N, 6.98; S, 7.83.

EXAMPLE 6

N-hydroxy-2-[[(4-methoxyphenyl)-sulfonyl]methyl]benzamide

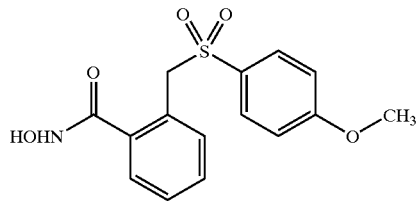

Part A: A 500 mL round bottom flask equipped with magnetic stir bar and $N_2$ inlet was charged with 1.5 mL (1.7 g, 12.0 mM) 4-methoxybenzenethiol and 2.5 g (10.9 mM) methyl (2-bromomethyl)benzoate in acetone (100 mL). The solution was treated with 1.8 g (13.1 mM) potassium carbonate and heated at 55° C. in an oil bath. The reaction mixture was stirred at 55° C. for 17 hrs, then concentrated in vacuo. The residue was partitioned between EtOAc and $H_2O$, the layers were separated and the aqueous layer was extracted with EtOAc (1x), the organic phases were combined, washed with 5% citric acid solution, saturated sodium bicarbonate solution and brine, dried ($Na_2SO_4$), and concentrated in vacuo to yield 3.3 g of product suitable for the next reaction.

Part B : A 500 mL round bottom flask equipped with magnetic stir bar and $N_2$ inlet was charged with 3.1 g (10.8 mM) of product from Part A in 90 mL MeOH. The solution was then treated with 15 mL water and 13.9 g (22.6 mM) Oxone®. The reaction mixture was stirred 17 hrs, then filtered. The filter cake was washed with MeOH, and the filtrate was concentrated in vacuo. The residue was partitioned between EtOAc and $H_2O$, the layers were separated and the aqueous layer was extracted with EtOAc (2x). The organic phases were combined, washed with saturated sodium bicarbonate solution and brine, dried ($MgSO_4$), and concentrated in vacuo to yield the 3.3 g of crude product. This was chromatographed on silica gel using 25–45% ethyl acetate/hexane to yield 2.1 g of pure product, m/z=321 (M+H).

Part C: A 250 mL round bottom flask equipped with magnetic stir bar and $N_2$ inlet was charged with 2.1 g (6.6 mM) of product from Part B in acetic acid (25 mL) and conc. HCl solution (25 mL) and the solution was heated to reflux for a total of 24 hours. The reaction mixture was concentrated in vacuo, then two aliquots of toluene were added and stripped, then dried under high vacuum to yield 2.0 g of product suitable for the next reaction.

Part D: A 2-necked 50 mL round bottom flask equipped with addition funnel, thermometer, magnetic stir bar and $N_2$ inlet was charged with 1.0 mL of DMF in 10 mL $CH_2Cl_2$. The solution was cooled in an ice bath, then treated with 3.5 mL (0.9 g, 6.9 mM) of a 2.0 M oxalyl chloride solution in $CH_2Cl_2$, then with a solution of 1.0 g (3.3 mM) of product from Part C in 5 mL DMF. The bath was removed and the reaction was stirred for 1 hour. This reaction mixture was added to a 2-necked 100 mL round-bottomed flask equipped with addition funnel, thermometer, magnetic stir bar and $N_2$ inlet and containing a cooled solution of 2.1 mL (1.1 g, 37.7 mM) of 50% aqueous hydroxylamine in THF (25 mL). The bath was then removed and the reaction mixture was stirred for 2 hours. The reaction was filtered, the filtrate was concentrated in vacuo, the residue was partitioned between EtOAc/water, the layers were separated, the aqueous layer was extracted with EtOAc (1x), the organic phases were combined and washed with water and brine, dried ($Na_2SO_4$) and concentrated in vacuo to yield 1.3 of crude product. This was chromatographed on silica gel using 80% ethyl acetate/hexane to yield 0.5 g of pure product, m/z=328 (M+Li).

EXAMPLE 7

N-hydroxy-2-[(4-methoxyanilino)-sulfonyl]benzamide

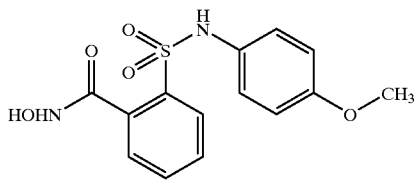

Part A: A 3-necked 100 mL round bottom flask equipped with addition funnel, thermometer, magnetic stir bar and $N_2$ inlet was charged with 0.5 g (4.3 mM) of p-anisidine and 1.8 mL (1.3 g, 12.8 mM) triethylamine in $CH_2Cl_2$ (20 mL). The solution was cooled in an ice bath, then treated with a solution of 1.0 g (4.3 mM) methyl (2-chlorosulfonyl)benzoate in $CH_2Cl_2$ (10 mL). The reaction mixture was stirred for 17 hrs, then concentrated in vacuo. The residue was partitioned between EtOAc and $H_2O$, the layers were separated and the organic phase was washed with 5% citric acid solution, saturated sodium bicarbonate solution and brine, dried ($Na_2SO_4$), and concentrated in vacuo to yield 0.9 g of crude product. This was chromatographed on silica gel using 20–30% ethyl acetate/hexane to yield 0.7 g of pure product, m/z=328 (M+Li).

Part B: A 100 mL round bottom flask equipped with magnetic stir bar and $N_2$ inlet was charged with 0.7 g (2.1 mM) of the product from Part A and 0.7 g (10.2 mM) of hydroxylamine hydrochloride in 10 mL MeOH. The reaction was cooled to 0¹C and charged with 0.4 g (16.4 mM) of sodium metal. After stirring for 17 hrs, the reaction was concentrated in vacuo, the residue was slurried in 20 mL of water, then acidified using 2N HCl solution. The aqueous slurry was extracted with EtOAc (3x). The organic layers were combined and washed with brine, dried ($Na_2SO_4$), and concentrated in vacuo to yield 0.6 g of crude product. The addition of methylene chloride to the crude product precipitated an off-white solid. Filtration gave 0.2 g of pure product, m/z=323 (M+Li).

EXAMPLE 8

N-hydroxy-2-[(benzylamino)-sulfonyl]benzamide

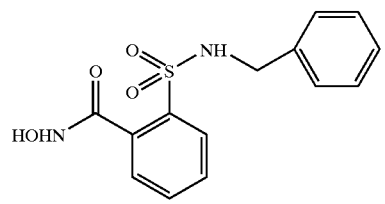

Part A: A 3-necked 100 mL round bottom flask equipped with addition funnel, thermometer, magnetic stir bar and $N_2$ inlet was charged with 0.5 mL (0.5 g, 4.3 mM) of benzylamine and 1.8 mL (1.3 g, 12.8 mM) triethylamine in $CH_2Cl_2$ (20 mL). The solution was cooled in an ice bath, then treated with a solution of 1.0 g (4.3 mM) methyl (2-chlorosulfonyl)benzoate in $CH_2Cl_2$ (10 mL). The reaction mixture was stirred for 2 hrs, then concentrated in vacuo. The residue was partitioned between EtOAc and $H_2O$, the layers were separated and the organic phase was washed with 5% citric acid solution, saturated sodium bicarbonate solution and brine, dried ($Na_2SO_4$), and concentrated in vacuo to yield 0.9 g of crude product. This was chromatographed on silica gel using 20% ethyl acetate/hexane to yield 0.7 g of pure product, m/z=312 (M+Li).

Part B: A 100 mL round bottom flask equipped with magnetic stir bar and $N_2$ inlet was charged with 0.7 g (2.1 mM) of the product from Part A and 0.7 g (10.6 mM) of hydroxylamine hydrochloride in 10 mL MeOH. The reaction was cooled to 0¹C and charged with 0.4 g (17.0 mM) of sodium metal. After stirring for 17 hrs, the reaction was concentrated in vacuo, the residue was slurried in 20 mL of water, then acidified using 2N HCl solution. The aqueous slurry was extracted with EtOAc (3x). The organic layers were combined and washed with brine, dried ($Na_2SO_4$), and concentrated in vacuo to yield 0.3 g of crude product. The addition of methylene chloride to the crude product precipitated a white solid. Filtration gave 0.1 g of pure product, m/z=307 (M+H).

EXAMPLE 9

In Vitro Metalloprotease Inhibition

The compounds prepared in the manner described in Examples 1 to 9 were assayed for activity by an in vitro assay. Following the procedures of Knight et al., *FEBS Lett.* 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$^2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 $\mu$M.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table (Table 38) below, reported in terms of $IC_{50}$ to three significant figures.

TABLE 38

| | Inhibition ($IC_{50}$ values in nM) | | |
|---|---|---|---|
| Example | MMP-13 | MMP-1 | MMP-2 |
| 1 | 45 | >10,000 | 10 |
| 2 | 2 | 900 | 0.3 |
| 3 | 1000 | >10,000 | 148 |
| 4 | >10,000 | >10,000 | >10,000 |
| 5 | >10,000 | >10,000 | 3500 |
| 6 | 4000 | >10,000 | — |
| 7 | >10,000 | >10,000 | — |
| 8 | >10,000 | >10,000 | — |

EXAMPLE 10 in Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea*; Kenyon, B M, et al., Investigative Ophthalmology & Visual Science, July 1996, Vol. 37, No. 8.

In this assay, uniformly sized Hydron™ pellets containing BFGF and sucralfate are prepared and surgically implanted into the stroma mouse cornea adjacent to the temporal limbus. The pellets are formed by making a suspension of 20

μL sterile saline containing 10 μg recombinant bFGF, 10 mg of sucralfate and 10 μL of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57Bl/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. an exemplary dose is 50 mg/kg bid, po. Neovascularization of the corneal stroma begins at about day three and is permitted to continue under the influence of the assayed compound until day five. At day five, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$\text{area} = \frac{(0.4 \times \text{clock hours} \times 3.14 \times \text{vessel length (in } mm))}{2}$$

The studied mice are thereafter compared to control mice and the difference in the area of neovascularization is recorded. A contemplated compound typically exhibits about 25 to about 75 percent inhibition, whereas the vehicle control exhibits zero percent inhibition.

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:

1. A compound or a salt thereof, wherein:
   the compound corresponds in structure to Formula V:

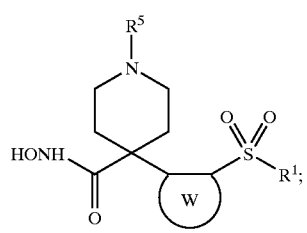

V the ring structure W is a 5- or 6-member divalent aromatic or heteroaromatic ring;

$R^1$ is a substituted 5- or 6-member cyclohydrocarbyl, heterocyclo, aryl, or heteroaryl radical that:
   has a length greater than about that of a hexyl group and less than about that of an eicosyl group, and
   $R^5$ is selected from the group consisting of $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl.

2. A compound or salt thereof according to claim 1, wherein the 5- or 6-member cyclohydrocarbyl, heterocyclo, aryl, or heteroaryl radical of $R^1$ is substituted with $R^4$, which has a chain length of from about 3 to about 14 carbon atoms.

3. A compound or salt thereof according to claim 2, wherein $R^4$ is selected from the group of substituents consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroaryl-heterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylhtiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio.

4. A compound or salt thereof according to claim 2, wherein $R^4$ is selected from the group of substituents consisting of phenyl, phenoxy, thiophenoxy, anilino, phenylazo, phenylureido, benzamido, nicotinamido, isonicotinamldo, picolinamido, heterocyclo, heterocyclohydrocarbyl, arylheterocyclohydrocarbyl, arylhydrocarbyl, heteroarylhydrocarbyl, heteroaryl-heterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio, wherein:
   any such substituent is substituted with one or more substituents independently selected from the group consisting of halogen, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylanmno, heterocyclic, heteroaryl, hydroxycarbonyl, hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonyl-hydrocarbyloxy, hydrocarbyloxy, carbonyl-hydrocarbyl, hydrocarbylhydroxycarbonyl, hydrocarbylthio, hydrocarbyloxycarbonyl-hydrocarbyloxy, hydrocarbyloxycarbonyl-hydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroaryl-carbonylamino, heteroarylhydrocarbylcarbonylamino, heterocyclohydrocarbyloxy, hydrocarbyl-sulfonylamino, arylsulfonylamino, arylhydrocarbylsulfonylamino, heteroarylsulfonylamino, heteroarylhydrocarbyl sulfonylamino, cyclohydrocarbylsulfonylamino, heterocyclohydrocarbylsulfonylamino, N-monosubstituted aminohydrocarbyl, and N,N-disubstituted aminohydrocarbyl, wherein:
  the substituent(s) on the monosubstituted or disubstituted aminohydrocarbyl nitrogen is/are independently selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or
  the substituents on the di-substituted aminohydrocarbyl nitrogen, together with the aminohydrocarbyl nitrogen, form a 5- to 8-member heterocyclic or heteroaryl ring.

5. A compound or a salt thereof, wherein:
the compound corresponds in structure to Formula V:

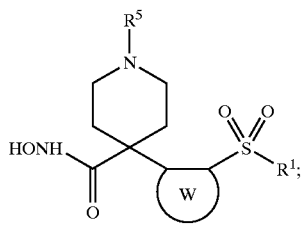

V the ring structure W is a 5- or 6-member divalent aromatic or heteroaromatic ring;
$R^1$ is a substituted 5- or 6-member cyclohydrocarbyl, heterocyclo, aryl, or heteroaryl radical substituted at its own 4-position when a 6-member ring or at its own 3-or 4-position when a 5-member ring with $R^4$;
$R^4$ is selected from the group consisting of single-ring cyclohydrocarbyl, single-ring heterocyclo, single-ring aryl, single-ring heteroaryl, $C_3$–$C_{14}$ hydrocarbyl, $C_2$–$C_{14}$ hydrocarbyloxy, phenoxy, thiophenoxy, 4-thiopyridyl, phenylazo, phenylureido, nicotinamido, isonicotinamido, picolinamido, anilino, and benzamido; and
$R^5$ is selected from the group consisting of $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl.

6. A compound or salt thereof according to claim 5, wherein $R^1$ has a length of from about greater than that of an octyl group to about less than that of a stearyl group.

7. A compound or salt thereof according to claim 5, wherein W is selected from the group consisting of 1,2-phenylene, 2,3-pryidinylene, 3,4-pyridinylene, 4,5-pyridinylene, 2,3-pyrazinylene, 4,5-pyrimidinylene, and 5,6-pyrimidinylene.

8. A compound or a salt thereof, wherein:
the compound corresponds in structure to Formula V:

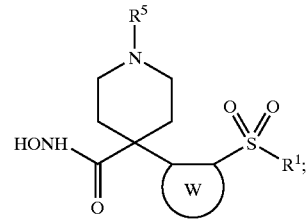

V the ring structure W is a 5- or 6-member divalent aromatic or heteroaromatic ring;
$R^1$ is phenyl substituted at its 4-position with $R^4$;
$R^4$ is selected from the group of substituents consisting of phenyl, phenoxy, thiophenoxy, phenylazo, benzamido, anilino, nicotinamido, isonicotinamido, picolinamido, and phenylureido, wherein any such substituent optionally is substituted:
  at the meta- or para-position or both with a moiety that is/are independently selected from the group consisting of halogen, $C_1$–$C_9$ hydrocarbyloxy group, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl, $C_1$–$C_4$ hydrocarbyl, $C_1$–$C_4$ hydrocarbyloxycarboflyl, $C_1$–$C_4$ hydrocarbyl and $C_1$–$C_8$-hydrocarbyl carboxamido, or
  at the meta- and para-positions by two methyl groups or a methylenedioxy group; and
$R^5$ is selected from the group consisting of $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl.

9. A process for treating a pathological condition treatable by the inhibition matrix metalloprotease activity in an animal, wherein:
the process comprises administering a compound or pharmaceutically acceptable salt thereof to the animal in an amount effective to treat the condition;
the compound corresponds in structure to Formula V:

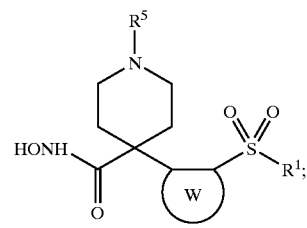

V the ring structure W is a 5- or 6-member divalent aromatic or heteroaromatic ring;
$R^1$ is a substituted 5- or 6-member cyclohydrocarbyl, heterocyclo, aryl, or heteroaryl radical that:
  has a length greater than about that of a hexyl group and less than about that of an eicosyl group, and
  $R^5$ is selected from the group consisting of $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl.

10. A process according to claim 9, wherein the 5- or 6-member cyclohydrocarbyl, heterocyclo, aryl, or heteroaryl radical of $R^1$ is substituted with $R^4$, which has a chain length of from about 3 to about 14 carbon atoms.

11. A process according to claim 10, wherein $R^4$ is selected from the group of substituents consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylbydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio.

12. A process according to claim 10, wherein $R^4$ is selected from the group of substituents consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio, wherein:
  any such substituent is substituted with one or more substituents independently selected from the group consisting of halogen, hydrocarbyl, hydrocarbyloxy, nitro, cyano, perfluorohydrocarbyl, trifluoromethylhydrocarbyl, hydroxy, mercapto, hydroxycarbonyl, axyloxy, arylthio, arylamino, arylhydrocarbyl, aryl, heteroaryloxy, heteroarylthio, heteroarylamino, heteroarhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylammo, arylhydrocarbyloxy, arylhydrocarbylthio, arylhydrocarbylamino, heterocyclic, heteroaryl, hydroxycarbonyl, hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxy, carbonylhydrocarbyl, hydrocarbylhydroxycarbonyl, hydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbyl sulfonylamino, cyclohydrocarbylsulfonylamino, heterocyclohydrocarbylsulfonylamino, N-rnonosubstituted aminohydrocarbyl, and N,N-disubstituted aminohydrocarbyl, wherein:
    the substituent(s) on the monosubstituted or disubstituted aminohydrocarbyl nitrogen is/are independently selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or
    the substituents on the di-substituted aminohydrocarbyl nitrogen, together with the aminohydrocarbyl nitrogen, form a 5- to 8-member heterocycic or heteroaryl ring.

13. A process fro treating a pathological condition treatable by the inhibition of matrix metalloprotease activity in an animal, wherein:
  the process comprises administering a compound or pharmaceutically acceptable salt thereof to the animal in an amount effective to treat the condition;
  the compound corresponds in structure to Formula V:

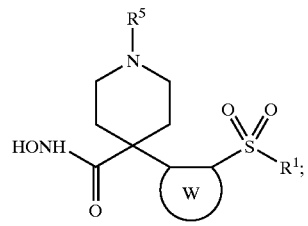

the ring structure W is a 5- or 6-member divalent aromatic or heteroaromatic ring;
  $R^1$ is a substituted 5- or 6member cyclohydrocarbyl, heterocyclo, aryl, or heteroaryl radical substituted at its own 4-position when a 6-member ring or at its own 3- or 4-position when a 5- member ring with $R^4$;
  $R^4$ is selected from the group consisting of single-ring cyclohydrocarbyl, single-ring heterocyclo, single-ring aryl, single-ring heteroaryl, $C_3$–$C_{14}$ hydrocarbyl, $C_2$–$C_{14}$ hydrocarbyloxy, phenoxy, thiophenoxy, 4-thiopyridyl, phenylazo, phenylureido, nicotinamido, isonicotinamido, picolinamido, anilino, and benzamido; and
  $R^5$ is selected from the group consisting of $C_1$–$C_4$ hydrocarbyl, $C_3$—$C_6$ cyclohydrocarbyl, $C_1$–$C_4$ acylhydrocarbyl, and sulfonyl $C_1$–$C_4$ hydrocarbyl.

14. A process according to claim 13, wherein $R^1$ has a length of from about greater than that of an octyl group to about less than that of a stearyl group.

15. A process according to claim 13, wherein the compound or pharmaceutically acceptable salt thereof is administered a plurality of times.

16. A process for treating a pathological condition treatable by the inhibition of matrix metalloprotease activity in an animal, wherein:
  the process comprises administering a compound or pharmaceutically acceptable salt thereof to the animal in an amount effective to treat the condition;

the compound corresponds in structure to Formula V:

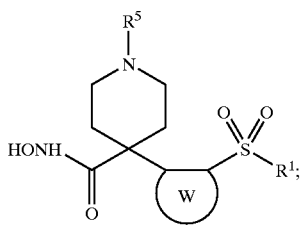

V the ring structure W is a 5- or 6-member divalent aromatic or heteroaromatic ring;
$R^1$ is phenyl substituted at its 4-position with $R^4$;
$R^4$ is selected from the group of substituents consisting of phenyl, phenoxy, thiophenoxy, phenylazo, benzamido, anilino, nicotinamido, isonicotinamido, picolinamido and phenylureido, wherein any such substituent optionally is substituted:
  at a meta- or para-position or both with a moiety that is/are independently selected from the group consisting of halogen, $C_1$–$C_9$ hydrocarbyloxy group, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl, $C_1$–$C_4$ hydrocarbyl, $C_1$–$C_4$ hydrocarbyloxycarbonyl, $C_1$–$C_4$ hydrocarbyl, and $C_1$–$C_8$-hydrocarbyl carboxamido, or
  at the meta- and para-positions by two methyl groups or a methylenedioxy group; and
$R^5$ is selected from the group consisting of $C_1$–$C_4$ hydrocarbyl, $C_3$–$C_6$ cyclohydrocarbyl, $C_1$–$C_4$ acylhydrocarbyl, and sulfonyl $C_1$–$C_4$ hydrocarbyl.

17. A process according to claim 16, wherein $R^4$ is selected from the group of substituents consisting of pheny, phenoxy, thiophenoxy, phenylazo, benzamido, anilino, nicotinamido, isonicotinamido, picolinamido, and phenylureido, wherein any such substituent is unsubstituted.

18. A pharmaceutical composition comprising a therapeutically effective amount of a compound or a salt thereof, wherein:
the compound corresponds in structure to Formula V:

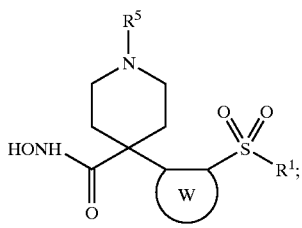

V the ring structure W is a 5- or 6-member divalent aromatic or heteroaromatic ring;
$R^1$ is a substituted 5- or 6-member cyclohydrocarbyl, heterocyclo, aryl, or heteroaryl radical that:
  has a length greater than about that of a hexyl group and less than about that of an eicosyl group, and
  $R^5$ is selected from the group consisting of $C_1$–$C_4$ hydrocarbyl, $C_3$–$C_6$ cyclohydrocarbyl, $C_1$–$C_4$ acylhydrocarbyl and sulfonyl $C_1$–$C_4$ hydrocarbyl.

19. A pharmaceutical composition according to claim 18, wherein the 5- or 6-member cyclohydrocarbyl, heterocyclo, aryl, or heteroaxyl radical of $R^1$ is substituted with $R^4$, which has a chain length of from about 3 to about 14 carbon atoms.

20. A pharmaceutical composition according to claim 19, wherein $R^4$ selected from the group of substituents consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylbydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio.

21. A pharmaceutical composition according to claim 19, wherein $R^4$ is selected from the group of substituents consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio, wherein:
  any such $R^4$ group is substituted with one or more substituents independently selected from the group consisting of halogen, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonyl, hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonyl-hydrocarbyloxy, hydrocarbyloxy, carbonyl-hydrocarbyl, hydrocarbylhydroxycarbonyl, hydrocarbylthio, hydrocarbyloxycarbonyl-hydrocarbyloxy, hydrocarbyloxycarbonylhydro-carbylthio, amino, hydrocarbylcarbonylamino, arylcarbonylamino, cyclohydrocarbylcarbonylamino, heterocyclohydrocarbylcarbonylamino, arylhydrocarbylcarbonylamino, hereroarylcarbonyl-amino, heteroarylhydrocarbylcarbonylamino, heterocyclohydrocarbyloxy, hydrocarbyl-sulfonylamino, arylsulfonylamino, arylhydro-carbylsulfonylamino, heteroarylsulfonylamino, heteroarylhydrocarbyl sulfonylamino, cyclo-hydrocarbylsulfonylamino, heterocyclohydro-carbylsulfonylamino, N-monosubstituted aminohydrocarbyl, and N,N-disubstituted aminohydrocarbyl, wherein:
the substituent(s) on the monosubstituted or disubstituted aminohydrocarbyl nitrogen is/are independently selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or
the substituents on the di-substituted aminohydrocarbyl nitrogen, together with the aminohydrocarbyl nitrogen itself, form a 5- to 8-member heterocyclic or heteroaryl ring.

22. A pharmaceutical composition comprising a therapeutically effective amount of a compound or a salt thereof, wherein:
the compound corresponds in structure to Formula V:

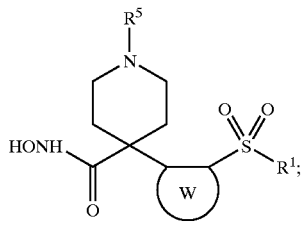

V the ring structure W is a 5- or 6-member divalent aromatic or heteroaromatic ring;
$R^1$ is a substituted 5- or 6-member cyclohydrocarbyl, heterocyclo, aryl, or heteroaryl radical substituted at its own 4-position when a 6-member ring or at its own 3- or 4-position when a 5-member ring with $R^4$;
$R^4$ is selected from the group consisting of single-ring cyclohydrocarbyl, single-ring heterocyclo, single-ring aryl, single-ring heteroaryl, $C_3-C_{14}$ hydrocarbyl, $C_2-C_{14}$ hydrocarbyloxy, phenoxy, thiophenoxy, 4-thiopyridyl, phenylazo, phenylureido, nicotinamido, isonicotinamido, picolinamido, anilino and benzamido; and
$R^5$ is selected from the group consisting of $C_1-C_4$ hydrocarbyl, $C_3-C_6$ cyclohydrocarbyl, $C_1-C_4$ acylhydrocarbyl, and sulfonyl $C_1-C_4$ hydrocarbyl.

23. A pharmaceutical composition according to claim 22, wherein $R^1$ has a length of from about greater than that of an octyl group to about less than that of a stearyl group.

24. A pharmaceutical composition according to claim 22, wherein W is selected from the group consisting of 1,2-phenylene, 2,3-pryldinylene, 3,4-pyridinylene, 4,5-pyridinylene, 2,3-pyrazinylene, 4,5-pyrimidinylene, and 5,6-pyrimidinylene.

25. A pharmaceutical composition comprising a therapeutically effective amount of a compound or a salt thereof, wherein:
the compound corresponds in structure to Formula V:

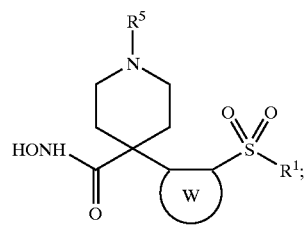

V the ring structure W is a 5- or 6-member divalent aromatic or heteroaromatic ring;
$R^1$ is phenyl substituted at its 4-position with $R^4$;
$R^4$ is selected from the group of substituents consisting of phenyl, phenoxy, thiophenoxy, phenylazo, benzamido, anilino, nicotinamido, isonicotinamido, picolinamdo and phenylureido, wherein any such substituent optionally is substituted:
at the meta- or para-position or both with a substituent that is/are independently selected from the group consisting of halogen, $C_1-C_9$ hydrocarbyloxy, $C_1-C_{10}$ hydrocarbyl, di-$C_1-C_9$ hydrocarbylamino, carboxyl $C_1-C_8$ hydrocarbyl, $C_1-C_4$ hydrocarbyloxy carbonyl, $C_1-C_4$ hydrocarbyl, $C_1-C_4$ hydrocarbyloxycarbonyl, $C_1-C_4$ hydrocarbyl, and $C_1-C_8$-hydrocarbyl carboxamido, or
at the meta- and para-positions by two methyl groups or a methylenedioxy group; and
$R^5$ is selected from the group consisting of $C_1-C_4$ hydrocarbyl, $C_3-C_6$ cyclohydrocarbyl, $C_1-C_4$ acylhydrocarbyl, and sulfonyl $C_1-C_4$ hydrocarbyl.

* * * * *